United States Patent
Kerschner et al.

(10) Patent No.: US 10,288,555 B2
(45) Date of Patent: May 14, 2019

(54) TAMPER SEAL DETECTION SYSTEM AND METHOD OF USE

(71) Applicant: THERMO FISHER SCIENTIFIC, INC., Waltham, MA (US)

(72) Inventors: Cody T. Kerschner, Fleetwood, PA (US); Christian S. Heaps, Emmaus, PA (US); Justin J. Tomel, Topton, PA (US); Shawn M. Regits, Catasauqua, PA (US)

(73) Assignee: Thermo Fisher Scientific, Inc., Waltham, MA (US)

( * ) Notice: Subject to any disclaimer, the term of this patent is extended or adjusted under 35 U.S.C. 154(b) by 0 days.

(21) Appl. No.: 15/786,238

(22) Filed: Oct. 17, 2017

(65) Prior Publication Data

US 2018/0113070 A1    Apr. 26, 2018

Related U.S. Application Data

(60) Provisional application No. 62/465,576, filed on Mar. 1, 2017, provisional application No. 62/412,008, filed on Oct. 24, 2016.

(51) Int. Cl.

| | |
|---|---|
| *G01N 21/00* | (2006.01) |
| *G01N 21/29* | (2006.01) |
| *B65D 55/02* | (2006.01) |
| *G01N 21/01* | (2006.01) |
| *G01N 21/63* | (2006.01) |
| *G09F 3/00* | (2006.01) |
| *G09F 3/03* | (2006.01) |
| *B07C 5/00* | (2006.01) |
| *B65B 51/00* | (2006.01) |

(Continued)

(52) U.S. Cl.
CPC ............ *G01N 21/29* (2013.01); *B07C 5/00* (2013.01); *B65B 51/00* (2013.01); *B65B 57/00* (2013.01); *B65D 55/02* (2013.01); *G01N 21/01* (2013.01); *G01N 21/63* (2013.01); *G01N 21/9009* (2013.01); *G01N 21/956* (2013.01); *G09F 3/0292* (2013.01); *G09F 3/03* (2013.01); *G01N 2021/0106* (2013.01)

(58) Field of Classification Search
CPC ............ G01N 21/909; G01N 21/9054; G01N 21/9036; G01N 21/90; B07C 5/3408
USPC ..................................................... 356/240.1
See application file for complete search history.

(56) References Cited

U.S. PATENT DOCUMENTS

| | | |
|---|---|---|
| 6,641,042 B1 | 11/2003 | Pierenkemper |
| 6,896,185 B2 | 5/2005 | Uhl |

(Continued)

OTHER PUBLICATIONS

European Search Report dated Mar. 12, 2018, issued in EP Application No. 17197850.5, filed Oct. 21, 2017.

(Continued)

*Primary Examiner* — Md M Rahman
(74) *Attorney, Agent, or Firm* — Workman Nydegger

(57) ABSTRACT

A tamper seal detection system for detecting a sealing sticker on a packaging box includes a housing at least partially bounding an inspection zone, the inspection zone being configured to receive the packaging box. A first sensor is configured to detect the presence of the first sealing sticker located on the packaging box when the packaging box is received within the inspection zone. A push guide is movable relative to the inspection floor between a first position and a spaced apart second position and can be used to push the packaging box out of the inspection zone.

18 Claims, 13 Drawing Sheets

(51) Int. Cl.
*B65B 57/00* (2006.01)
*G01N 21/90* (2006.01)
*G01N 21/956* (2006.01)

(56) References Cited

U.S. PATENT DOCUMENTS

| | | |
|---|---|---|
| 7,215,363 B2 | 5/2007 | Stamm |
| 8,248,620 B2 | 8/2012 | Wicks |
| 2007/0296963 A1 | 12/2007 | Parker |
| 2009/0009192 A1 | 1/2009 | Farrelly et al. |
| 2010/0013500 A1 | 1/2010 | Maher et al. |
| 2013/0008962 A1 | 1/2013 | Anand |
| 2013/0161159 A1 | 6/2013 | Fisher et al. |
| 2015/0241360 A1 | 8/2015 | Niemela |

OTHER PUBLICATIONS

Keyence brochure, *Full-Spectrum Sensor, Stable Detection of Changes in Appearance*, LR-W Series, 2016, pp. 36.

TAMPER SEAL DETECTION SYSTEM AND METHOD OF USE

CROSS-REFERENCE TO RELATED APPLICATIONS

This application claims the benefit of Provisional Application No. 62/465,576, filed Mar. 1, 2017, and Provisional Application No. 62/412,008, filed Oct. 24, 2016, which are incorporated herein by specific reference.

BACKGROUND OF THE INVENTION

1. The Field of the Invention

The present invention relates to tamper seal detection systems used in inspecting the packaging of drugs for blinded clinical trials and methods of using such systems.

2. The Relevant Technology

Clinical trials for many pharmaceutical drugs require that a drug and a placebo be delivered and administered in a blinded study. As part of the blinded clinical trial protocols, the drug and placebo are placed in separate unmarked containers. Accordingly, the administering technician and recipient are blind as to the identity of the product, the concentration thereof, or other characteristic being studied that may otherwise be reported on the retail label of the drug container.

To facilitate transport and delivery of the drug/placebo, the unmarked containers can be sealed in a box. For instance, an unmarked dosage vial or tube can be placed in a box having a lid that can be folded over to close the box. Once the lid is closed, a sealing sticker is manually placed on the outside of the box so as to extend between the lid and the body of the box, thereby fixing the lid closed and sealing the contents therein. The unbroken sealing sticker indicates that the box has not been opened following sealing of the product therein. The box can also be marked with a label that includes an identification number or other information associated with the included product. However, this identifying information is keyed to a reference list and is only useful in identifying the product in combination with that list. Accordingly, the box may also lack any direct, product-identifying marks or labels to ensure fidelity of the blinded study.

The packaging of the drug/placebo is typically performed in large batches. For example, a single continuous run may package desired dosages of drugs and/or placebos within 4,000 different boxes. Packaging protocols for blinded clinical trials require that an inspection process be used to ensure that sealing sticker(s) are applied to every box. One inspection process comprises counting the actual number of sealing stickers used and comparing it to the number so stickers that should have been used. For example, some boxes require two stickers, one on the top and one on the bottom, to properly seal the box. Thus, if 4,000 boxes are packaged, 8,000 stickers should have been used. The problem with this approach, however, is that if the sticker count is off by one, all of the 4,000 boxes may need to be inspected to ensure that all of the boxes are properly sealed and determine why the count is off. As can be appreciated, such an inspection can be labor intensive, time consuming, and potential subject to human error. Similar problems also exist with other inspection processes.

Accordingly, what is needed in the art are systems and methods for more accurately and efficiently inspecting boxes containing drugs or placebos used in blinded clinical studies to ensure that they are properly sealed.

SUMMARY OF THE INVENTION

In a first independent aspect of the present invention, a tamper seal detection system for detecting a sealing sticker on a packaging box includes:
  a housing at least partially bounding an inspection zone that is configured to receive a packaging box having one or more sealing stickers thereon; and
  a first sensor configured to detect the presence of a first sealing sticker located on the packaging box when the packaging box is received within the inspection zone, the first sensor being mounted on the housing so as to detect through a first side of the inspection zone, the first sensor being adjustable mounted on the housing so that the first sensor can be moved in at least one dimension.

In one embodiment, the first sensor is adjustable mounted on the housing so that the first sensor can be moved in at least two dimensions.

In one embodiment, first sensor is adjustable mounted on the housing so that the first sensor can be moved in three dimensions.

In another embodiment, a second sensor is configured to detect the presence of a second sealing sticker located on the packaging box when the packaging box is received within the inspection zone, the second sensor being mounted on the housing so as to detect through a second side of the inspection zone that is opposite the first side.

In another embodiment, the second sensor is adjustably mounted on the housing so that the second sensor can be moved in at least two dimensions.

In another embodiment, the first side of the inspection zone comprises an upper side of the inspection zone and the second side of the inspection zone comprises a lower side of the inspection zone, lower side being vertically below the upper side.

In another embodiment, the first side of the inspection zone comprises a right side of the inspection zone and the second side of the inspection zone comprises a left side of the inspection zone, wherein the left side is laterally spaced apart from the right side.

In another embodiment, the housing comprises an inspection floor, at least a portion of the inspection floor being transparent, the inspection floor being disposed between the first sensor and the inspection zone.

In another embodiment, a first guide rail and a laterally spaced apart second guide rail are disposed on the inspection floor.

In another embodiment, at least one of the first guide rail and the second guide rail can be selectively moved laterally.

In another embodiment, the housing comprises a base that includes the inspection floor and a support structure upstanding from the base, the inspection zone being disposed above the inspection floor and at least partially bounded by the support structure.

In another embodiment, a gate is secured to the housing, the gate being movable between a closed position wherein the gate restricts withdrawal of the packaging box from the inspection zone and an open position wherein the packaging box is free to pass out of the inspection zone.

In another embodiment, the gate raises and lowers, pivots, slides, or rolls and unrolls as the gate moves between the open and closed position.

In another embodiment, an electronic controller is in electrical communication with the gate and the first sensor.

In another embodiment, a notice generator is in electrical communication with the electronic controller.

In another embodiment, the notice generator comprises a light source or sound generator.

In another embodiment, the invention further comprises:
an electronic controller in electrical communication with the gate and the first sensor, the controller being programmed to perform the following functions:
activating the first sensor to determine whether the first sealing sticker is located on a first side of the packaging box that is located within the inspection zone; and
sending a signal to the gate which causes the gate to move from the closed position to the open position if the first sensor detects the presence of the first sealing sticker.

In another embodiment, a handle is mounted on the housing for use in manually carrying the tamper seal detection system.

In another embodiment, the tamper seal detection system has a total weight of less than 45 kilograms (kg) and more commonly less than 35 kg, 25 kg, or 15 kg.

In another embodiment, the housing has a height, width, and depth each having a maximum dimension of less than 1.5 meters and more commonly less than 1.25 meters, 1 meter, 0.75 meters or 0.5 meters.

In another embodiment, the first sensor can detect the shape, size, color, location, or orientation of a sealing sticker.

In another embodiment, a conveyor belt is passing through the inspection zone.

In another embodiment, the conveyor belt has an opening passing therethrough so that when the packaging box is positioned on the conveyor belt, the first sensor can detect a sealing sticker located on the packaging box through the opening.

In another embodiment, the housing comprises a sloped ramp leading to the inspection zone.

In another embodiment, the packaging box is disposed within the inspection zone, the packaging box being sealed closed by the at least one or more sealing stickers thereon.

In another embodiment, a blinded trial product is disposed within the packaging box.

In another embodiment, the first sensor is an optical sensor.

In another embodiment, the first sensor is a luminescence sensor.

The first aspect of the invention may also include any of the features, options and possibilities set out elsewhere in this document, including those in or associated with the below discussed second through sixth aspects of the invention.

In a second independent aspect of the present invention, a method for detecting sealing stickers on a packaging box includes:
inserting a first packaging box into an inspection zone of a tamper seal detection system, the first packaging box having a first sealing sticker thereon that at least partially seals the first packaging box closed; and
activating a first optical sensor of the tamper seal detection system to detect whether the first sealing sticker is located on a first side of the first packaging box.

In one embodiment, the first packaging box is inserted into the inspection zone so that the first packaging box is disposed between a pair of guide rails and adjacent to a gate, the gate being movable between an open and closed position.

In another embodiment, prior to the step of inserting the first packaging box the method comprises:
inserting a blinded trial product into a compartment of the first packaging box; folding the first packaging box into a closed position; and
applying the first sealing sticker to the packaging box so as to at least partially seal the packaging box closed.

In another embodiment, the blinded trial product comprises an active drug product, a comparative drug product, a control drug product, or a placebo product.

In another embodiment, the method further includes manually adjusting the position of the first optical sensor before inserting a first packaging box into the inspection zone.

In another embodiment, the first optical sensor is adjusted in two dimensions.

In another embodiment, the first optical sensor is a luminescence sensor.

In a sub-aspect of the present invention, the method further includes:
the first packaging box being inserted into the inspection zone through a first side of the inspection zone; and
removing the first packaging box from the inspection zone through a second side of the inspection zone if the first optical sensor detects that the first sealing sticker is located on a first side of the first packaging box.

In one embodiment, the method further includes removing the first packaging box through the first side of the inspection zone if the first optical sensor detects that the first sealing sticker is not located on the first side of the first packaging box.

In another embodiment, the tamper seal detection system comprises a gate in a closed position which restricts the first packaging box from being removed from the inspection zone through the second side, the method further comprising an electronic controller moving the gate to an open position so that the first packaging box can be removed from the inspection zone through the second side of the inspection zone when the first optical sensor detects that the first sealing sticker is located on a first side of the first packaging box, the electronic controller being in electrical communication with the first optical sensor.

In another embodiment, the gate is moved to the open position by raising, lower, rolling, sliding or pivoting the gate.

In another embodiment, the first packaging box has a second sealing sticker thereon that at least partially seals the first packaging box closed, the method further comprising activating a second optical sensor of the tamper seal detection system to detect whether the second sealing sticker is located on a second side of the first packaging box.

In another embodiment, the tamper seal detection system comprises an electronic controller in electrical communication with the first optical sensor, the electronic controller being programmed to generate a notice signal when the first optical sensor detects that the first sealing sticker is located on the first side of the first packaging box.

In another embodiment, the tamper seal detection system comprises an electronic controller in electrical communication with the first optical sensor, the electronic controller being programmed to generate a notice signal when the first optical sensor detects that the first sealing sticker is not located on the first side of the first packaging box.

In another embodiment, the method further includes moving a push guide of the tamper seal detection system from a first position to a second position if the first optical sensor detects that the first sealing sticker is located on the first side of the first packaging box, the push guide moving the first packaging box at least partially out of the inspection zone as the push guide is moved from the first position to the second position.

In another embodiment, a proximity sensor is detecting the presence of the first packaging box when the first packaging box is moved to the at least partially out of the inspection zone.

In another embodiment, the method further includes:
returning the push guide to the first position; and
placing a second packaging box in the inspection zone.

In another embodiment, the push guide and the first optical sensor are controlled by an electrical controller.

In another embodiment, the method includes not moving the push guide if the first optical sensor detects that the first sealing sticker is not located on the first side of the first packaging box until after the first packaging box is removed from the inspection zone.

In another embodiment, the method further includes opening a gate of the tamper seal detection system if the first optical sensor detects that the first sealing sticker is located on the first side of the first packaging box.

In another embodiment, the step of inserting the first packaging box comprises placing the first packaging box on an inspection floor of the tamper seal detection system so that the first packaging box abuts against a push guide that is movable relative to the inspection floor.

In another embodiment, the push guide has a rear guide face against which a first side of the packaging box abuts and a side guide face against which a second side of the packaging box abuts.

In another embodiment, the rear guide face is orthogonal to the side guide face.

In another embodiment, the first optical sensor detects the first sealing sticker based on the color, size, shape, or orientation of the first sealing sticker or indicia disposed on the first sealing sticker.

In another embodiment, the first optical sensor detects whether the first sealing sticker is located within a specific predefined area on the first side of the packaging box.

In another embodiment, the first optical sensor detects whether the first sealing sticker is orientated in a specific predefined orientation on the first side of the packaging box.

In another embodiment, the step of inserting the first packaging box comprises:
placing the first packaging box on a conveyor belt having an opening extending therethrough, the first packaging box being positioned so that the first sealing sticker secured to the first packaging is visible through the opening; and
moving the conveyor belt so that the conveyer belt moves first packaging box to the inspection zone.

In another embodiment, a proximity sensor detects the presence of the first packaging box when the first packaging box is inserted into the inspection zone.

The second aspect of the invention may also include any of the features, options and possibilities set out elsewhere in this document, including those in or associated with the above first aspect of the invention and the below discussed third through sixth aspects of the invention.

In a third independent aspect of the present invention, a method for detecting tamper seals on a packaging box includes:

inserting a first packaging box into an inspection zone of a tamper seal detection system;
activating a first optical sensor of the tamper seal detection system to detect whether a first sealing sticker is located on a first side of the first packaging box;
removing the first packaging box from the inspection zone;
adjusting the position of the first sensor of the tamper seal detection system;
inserting a second packaging box into the inspection zone of the tamper seal detection system, the second packaging box being a different size or shape than the first packaging box; and
activating the first sensor of the tamper seal detection system to detect whether a first sealing sticker is located on a side of the second packaging box.

The third aspect of the invention may include any of the features, options and possibilities set out elsewhere in this document, including those in or associated with the above first and second aspects of the invention and the below discussed fourth through sixth aspects of the invention.

In a fourth independent aspect of the present invention, a tamper seal detection system for inspecting a packaging box containing a blinded trial product, the system comprising:
a housing at least partially bounding an inspection zone, the packaging box being received within the inspection zone; and
a first optical sensor disposed on the housing;
a gate disposed on the housing;
an electronic controller in electrical communication with the first optical sensor and the gate, the electronic controller being programmed to perform the following functions:
use the first optical sensor to determine whether a sealing sticker that is used to at least partially seal the packaging box closed is located on the packaging box; and
move the gate from a closed position to an open position if the electronic controller determines that the sealing sticker is located on the packaging box.

In one embodiment, the electronic controller performs the function of using the first optical sensor to determine whether the sealing sticker is located within a predefined area on the packaging box or within a predefined distance from a predefined location on the packaging box.

In another embodiment, the electronic controller performs the function of generating a notice signal if the electronic controller determines that the sealing sticker is not located on the packaging box.

In another embodiment, the electronic controller performs the function moving a conveyor belt supporting the packaging box to remove the packaging box from the inspection zone after the gate is moved to the open position.

In another embodiment, the electronic controller performs the function of recording an identifier for the packaging box.

The fourth aspect of the invention may also include any of the features, options and possibilities set out elsewhere in this document, including those in or associated with the above first through third aspects of the invention and the below discussed fifth and sixth aspects of the invention.

In a fifth independent aspect of the present invention, a tamper seal detection system for inspecting a packaging box containing a blinded trial product includes:
a housing having an inspection floor and at least partially bounding an inspection zone, the packaging box being disposed on the inspection floor so as to be received within the inspection zone;

a first optical sensor disposed on the housing;
a push guide at least partially disposed above the inspection floor; and
an electronic controller in electrical communication with the first optical sensor and the push guide, the electronic controller being programmed to perform the following functions:
use the first optical sensor to determine whether a sealing sticker that is used to at least partially seal the packaging box closed is located on the packaging box; and
move the push guide from a first position to a second position so that the push guide at least partially moves the packaging box out of the inspection zone if the electronic controller determines that the sealing sticker is located on the packaging box.

In one embodiment, the electronic controller performs the function of moving a gate from a closed position to an open position if the electronic controller determines that the sealing sticker is located on the packaging box.

In another embodiment, the electronic controller performs the function of using the first optical sensor to determine whether the sealing sticker is located within a predefined area on the packaging box or within a predefined distance from a predefined location on the packaging box.

In another embodiment, the electronic controller performs the function of generating a notice signal if the electronic controller determines that the sealing sticker is not located on the packaging box.

In another embodiment, a first proximity sensor is disposed on the housing.

The fifth aspect of the invention may also include any of the features, options and possibilities set out elsewhere in this document, including those in or associated with the above first through fourth aspects of the invention and the below discussed sixth aspects of the invention.

In a sixth independent aspect of the present invention, a tamper seal detection system for detecting a sealing sticker on a packaging box includes:
a housing having an inspection floor and at least partially bounding an inspection zone, the inspection zone being configured to receive a packaging box having one or more sealing stickers thereon;
a first sensor configured to detect the presence of a first sealing sticker located on the packaging box when the packaging box is received within the inspection zone, the first sensor being mounted on the housing; and
a push guide assembly comprising a push guide that is at least partially disposed above the inspection floor, the push guide being movable relative to the inspection floor between a first position and a spaced apart second position.

In one embodiment, when the packaging box is disposed on the inspection floor and biased against the push guide, the push guide moves the packaging box as the push guide is moved between the first position and the second position.

In another embodiment, the packaging box is moved from the inspection zone to a location at least partially spaced apart from the inspection zone as the push guide is moved between the first position and the second position.

In another embodiment, the push guide has a rear guide face that butts against a first side of the packaging box and a side guide face that butts against a second side of the packaging box when the packaging box is disposed on the inspection floor.

In another embodiment, the side guide face is orthogonal to the rear guide face.

In another embodiment, the push guide comprises an L-shaped body having a rear arm with a rear guide face and a side arm with a side guide face.

In another embodiment, the push guide assembly further comprises a drive assembly that moves the push guide between the first position and the second position.

In another embodiment, the drive assembly is at least partially disposed below the inspection floor.

In another embodiment, the push guide assembly further comprises means for moving the push guide between the first position and the second position.

In another embodiment, at least a portion of the inspection floor is transparent, the first sensor being disposed below the inspection floor.

In another embodiment, a second sensor is configured to detect the presence of a second sealing sticker located on the packaging box when the packaging box is received within the inspection zone, the second sensor being mounted on the housing.

In another embodiment, the second sensor is located above the inspection floor.

In another embodiment, the first sensor is adjustably mounted on the housing so that the first sensor can be moved in at least two dimensions.

In another embodiment, a gate is secured to the housing, the gate being movable between a closed position wherein the gate restricts withdrawal of the packaging box from the inspection zone and an open position wherein the packaging box is free to pass out of the inspection zone.

In another embodiment, the gate moves from the closed position to the open position as the push guide moves from the first position to the second position.

In another embodiment, the gate raises and lowers, pivots, slides, or rolls and unrolls as the gate moves between the open and closed position.

In another embodiment, an electronic controller is in electrical communication with the gate, the first sensor and the push guide assembly.

In another embodiment, a notice generator is in electrical communication with the electronic controller.

In another embodiment, the notice generator comprises a light source or sound generator.

In another embodiment, the invention further includes:
an electronic controller in electrical communication with the push guide assembly and the first sensor, the controller being programmed to perform the following functions:
activating the first sensor to determine whether the first sealing sticker is located on a first side of the packaging box that is located within the inspection zone; and
sending a signal to the push guide assembly which causes the push guide to move from the first position to the second position if the first sensor detects the presence of the first sealing sticker.

In another embodiment, the first sensor can detect the shape, size, color, location, or orientation of a sealing sticker.

In another embodiment, the packaging box is disposed within the inspection zone, the packaging box being sealed closed by the at least one or more sealing stickers thereon.

In another embodiment, a blinded trial product is disposed within the packaging box.

In another embodiment, the first sensor is an optical sensor.

In another embodiment, the first sensor is a luminescence sensor.

In another embodiment, a proximity sensor is disposed on the housing and is configured to detect the presence of the packaging box when the packaging box is received within the inspection zone.

The sixth aspect of the invention may also include any of the features, options and possibilities set out elsewhere in this document, including those in or associated with the above first through fifth aspects of the invention.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
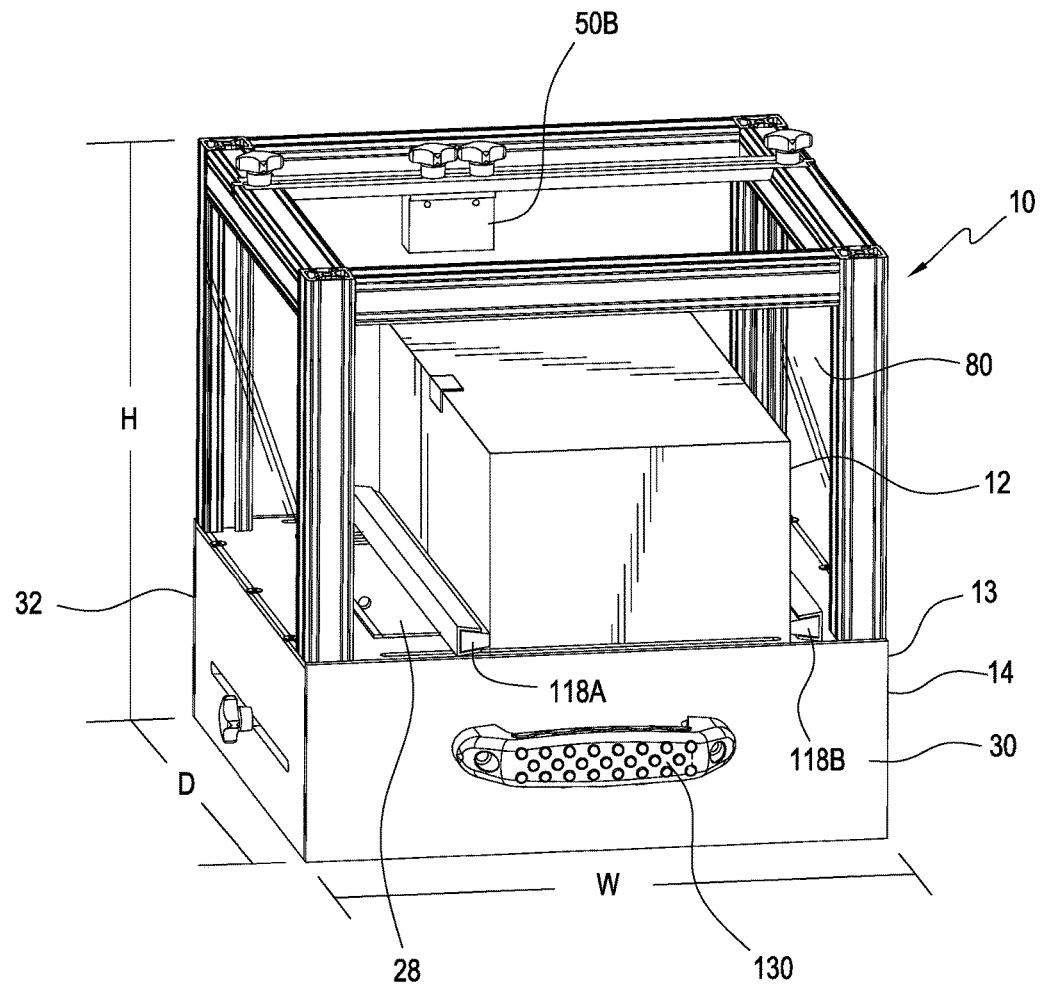
FIG. 1 is a perspective view of a tamper seal detection system housing a packaging box.

Before describing the present disclosure in detail, it is to be understood that this disclosure is not limited to parameters of the particularly exemplified systems, methods, apparatus, products, processes, compositions, and/or kits, which may, of course, vary. It is also to be understood that the terminology used herein is only for the purpose of describing particular embodiments of the present disclosure, and is not necessarily intended to limit the scope of the disclosure in any particular manner. Thus, while the present disclosure will be described in detail with reference to specific embodiments, features, aspects, configurations, etc., the descriptions are illustrative and are not to be construed as limiting the scope of the claimed invention. Various modifications can be made to the illustrated embodiments, features, aspects, configurations, etc. without departing from the spirit and scope of the invention as defined by the claims. Thus, while various aspects and embodiments have been disclosed herein, other aspects and embodiments are contemplated.

Unless defined otherwise, all technical and scientific terms used herein have the same meaning as commonly understood by one of ordinary skill in the art to which the present disclosure pertains. While a number of methods and materials similar or equivalent to those described herein can be used in the practice of the present disclosure, only certain exemplary materials and methods are described herein.

Various aspects of the present disclosure, including devices, systems, methods, etc., may be illustrated with reference to one or more exemplary embodiments or implementations. As used herein, the terms "embodiment," "alternative embodiment" and/or "exemplary implementation" means "serving as an example, instance, or illustration," and should not necessarily be construed as preferred or advantageous over other embodiments or implementations disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an" and "the" include plural referents unless the content clearly dictates otherwise. Thus, for example, reference to a "panel" includes one, two, or more panels. Similarly, reference to a plurality of referents should be interpreted as comprising a single referent and/or a plurality of referents unless the content and/or context clearly dictate otherwise. Thus, reference to "panels" does not necessarily require a plurality of such panels. Instead, it will be appreciated that independent of conjugation; one or more panels are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

Various aspects of the present disclosure can be illustrated by describing components that are coupled, attached, connected, and/or joined together. As used herein, the terms "coupled", "attached", "connected," and/or "joined" are used to indicate either a direct connection between two components or, where appropriate, an indirect connection to one another through intervening or intermediate components. In contrast, when a component is referred to as being "directly coupled", "directly attached", "directly connected," and/or "directly joined" to another component, no intervening elements are present or contemplated. Thus, as used herein, the terms "connection," "connected," and the like do not necessarily imply direct contact between the two or more elements. In addition, components that are coupled, attached, connected, and/or joined together are not necessarily (reversibly or permanently) secured to one another. For instance, coupling, attaching, connecting, and/or joining can comprise placing, positioning, and/or disposing the components together or otherwise adjacent in some implementations.

As used herein, directional and/or arbitrary terms, such as "top," "bottom," "front," "back," "left," "right," "up," "down," "upper," "lower," "inner," "outer," "internal," "external," "interior," "exterior," "proximal," "distal" and the like can be used solely to indicate relative directions and/or orientations and may not otherwise be intended to limit the scope of the disclosure, including the specification, invention, and/or claims.

Where possible, like numbering of elements have been used in various figures. In addition, similar elements and/or elements having similar functions may be designated by similar numbering (e.g., element "10" and element "210.") Furthermore, alternative configurations of a particular element may each include separate letters appended to the element number. Accordingly, an appended letter can be used to designate an alternative design, structure, function, implementation, and/or embodiment of an element or feature without an appended letter. Similarly, multiple instances of an element and or sub-elements of a parent element may each include separate letters appended to the element number. In each case, the element label may be used without an appended letter to generally refer to instances of the element or any one of the alternative elements. Element labels including an appended letter can be used to refer to a specific instance of the element or to distinguish or draw attention to multiple uses of the element. However, element labels including an appended letter are not meant to be limited to the specific and/or particular embodiment(s) in which they are illustrated. In other words, reference to a specific feature in relation to one embodiment should not be construed as being limited to applications only within said embodiment.

It will also be appreciated that where a range of values (e.g., less than, greater than, at least, and/or up to a certain value, and/or between two recited values) is disclosed or recited, any specific value or range of values falling within the disclosed range of values is likewise disclosed and contemplated herein. Thus, disclosure of an illustrative measurement or distance less than or equal to about 10 units or between 0 and 10 units includes, illustratively, a specific disclosure of: (i) a measurement of 9 units, 5 units, 1 units, or any other value between 0 and 10 units, including 0 units and/or 10 units; and/or (ii) a measurement between 9 units and 1 units, between 8 units and 2 units, between 6 units and 4 units, and/or any other range of values between 0 and 10 units.

It is also noted that systems, methods, apparatus, devices, products, processes, compositions, and/or kits, etc., according to certain embodiments of the present invention may include, incorporate, or otherwise comprise properties, features, aspects, steps, components, members, and/or elements described in other embodiments disclosed and/or described herein. Thus, reference to a specific feature, aspect, steps, component, member, element, etc. in relation to one embodiment should not be construed as being limited to applications only within said embodiment. In addition, reference to a specific benefit, advantage, problem, solution, method of use, etc. in relation to one embodiment should not be construed as being limited to applications only within said embodiment.

The headings used herein are for organizational purposes only and are not meant to be used to limit the scope of the description or the claims. To facilitate understanding, like reference numerals have been used, where possible, to designate like elements common to the figures.

The present invention relates to tamper seal detection systems that can be used as part of an inspection process to determine, in part, whether sealing stickers are located and/or properly positioned on packaging boxes containing blinded trial product used in blinded trials. In other embodiments, the tamper seal detection systems can be used to determine whether sealing stickers are located and/or properly positioned on packaging boxes containing products not used in blinded trials but where it is desired to inspect the proper application of sealing stickers. Furthermore, the tamper seal detection systems can also be used to determine whether select labels are applied to or select indicia is printed on packaging boxes, whether or not used for blinded trials, and can process and store information from such labels or indicia.

Figure 2:
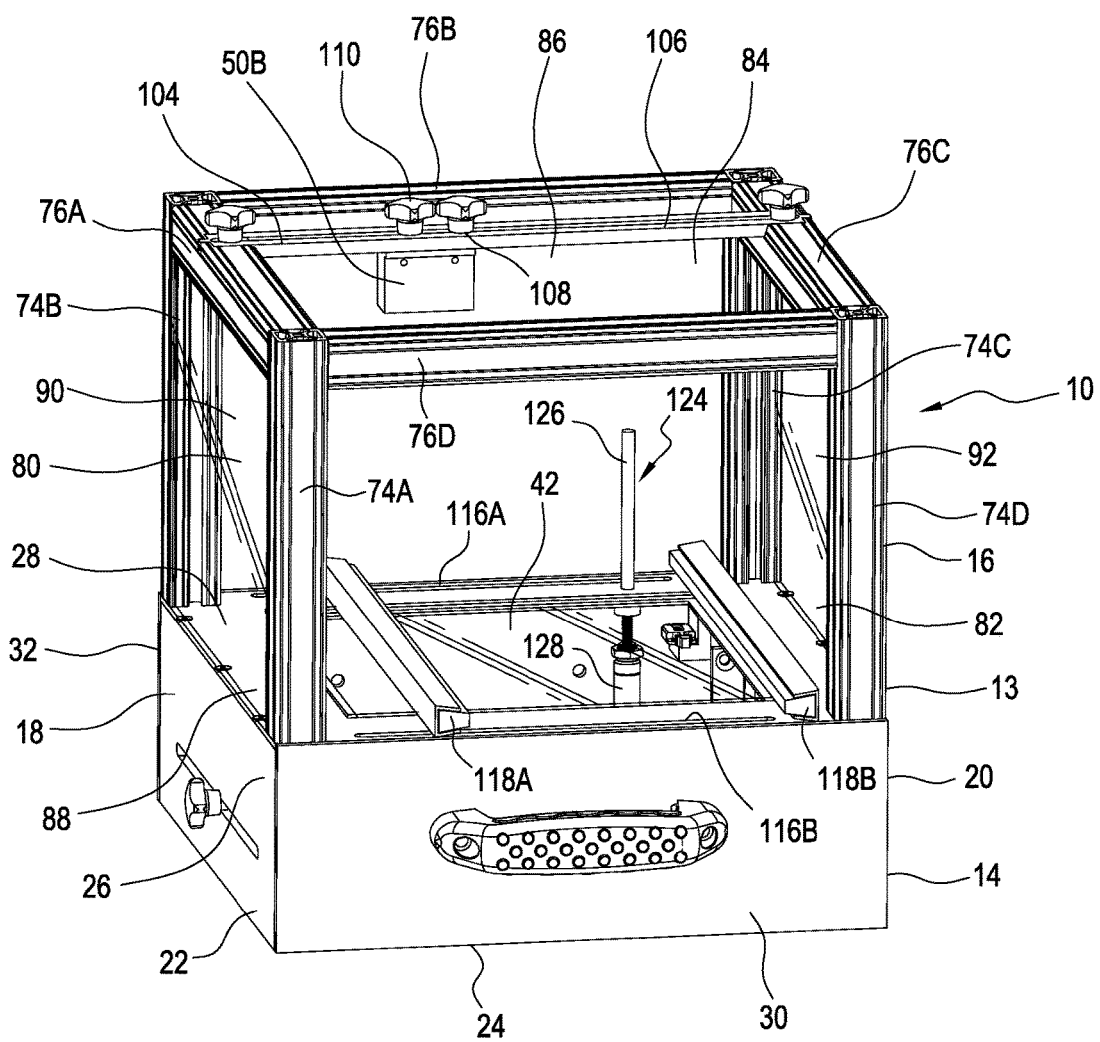
FIG. 2 is a perspective view of the tamper seal detection system depicted in FIG. 1 with the packaging box removed therefrom.
Figure 3:
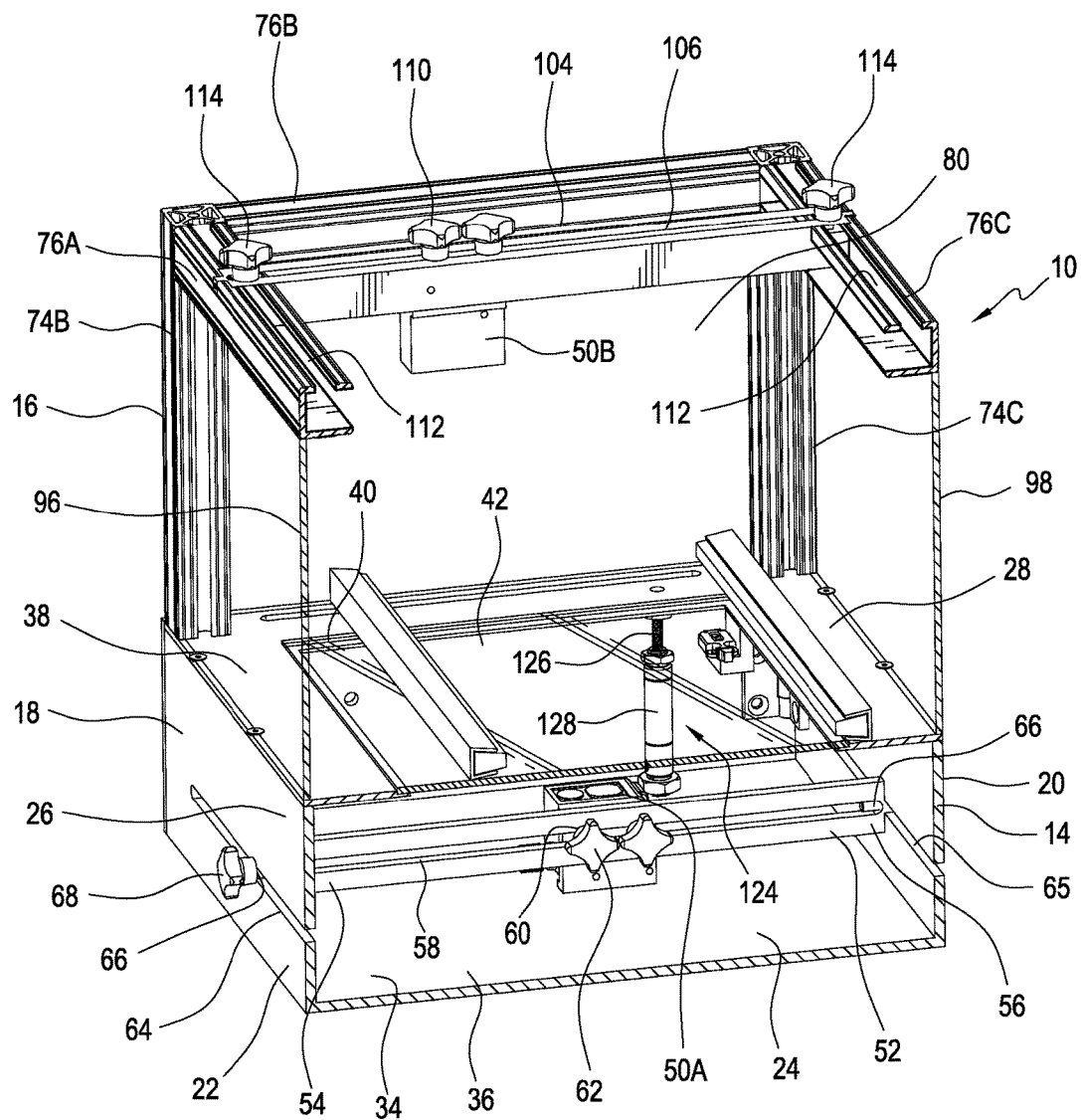
FIG. 3 is a cross sectional front view of the tamper seal detection system depicted in FIG. 2 with the gate thereof in an open position.

By way of example and not by limitation, depicted in FIG. 1 is one embodiment of a tamper seal detection system 10 incorporating features of the present invention and used to detect sealing stickers on a packaging box 12. As depicted in FIGS. 2 and 3, tamper seal detection system 10 comprises a housing 13 that includes a base 14 and a support structure 16 disposed on base 14. Base 14 comprises a first side wall 18 and a spaced apart second side wall 20 each having a lower end 22 and an opposing upper end 26. A base floor 24 extends between side walls 18 and 20 at lower ends 22 while an inspection floor 28 extends between side walls 18 and 20 at upper ends 26. When resting on a horizontal surface, side walls 18 and 20 are typically vertically extending while base floor 24 and inspection floor 28 are horizontally disposed. Base 14 also includes a front wall 30 and an opposing back wall 32 disposed at opposing ends of side walls 18 and 20 and between which base floor 24 and inspection floor 28 extend. Base 4 has an interior surface 34 that bounds a compartment 36.

Inspection floor 28 is depicted as comprising a support portion 38 which extends around a perimeter of inspection floor 28 and which bounds an opening 40 that extends through inspection floor 28 and communicates with compartment 36. Disposed within opening 40 so as to be supported by support portion 38 is a transparent panel 42. Panel 42 can be made of a transparent glass, plastic, or other material. Support portion 38 is typically made of an opaque material such as an opaque metal or plastic. In other embodiments, all of inspection floor 28 can be formed of a transparent material. For example, inspection floor 28 could comprise a single transparent panel that is supported by walls 18, 20, 28 and 30. In other embodiments, support portion 38 may only extend around a portion of the perimeter of inspection floor 28 and thus only partially bound opening 40. In this embodiment, a portion of transparent panel 42 may be directly supported by one or more of walls 18, 20, 28 and 30. Other configurations can also be used.

Disposed within compartment 36 is an optical sensor 50A. As discussed below in greater detail, optical sensor 50A can be programmed to detect the presence of sealing stickers located on packaging box 12 when packaging box 12 is supported on inspection floor 28 of housing 13. In one embodiment, optical sensor 50A and the other optical sensors 50 discussed herein can comprise a luminescence sensor that emits UV light. Luminescence sensors detect visible and non-visible marks that illuminate when using ultraviolet (UV) light. Fluorescent material and marks are reliably detected independently of their pattern, colors or surface conditions on any material. Luminescence sensors emit UV light with a wavelength of approximately 375 nm. Fluorescent substances convert the UV light into long-wave visible light, which is then received and evaluated by the luminescence sensor.

One specific example of luminescence sensors that can be used for optical sensor 50A and the other optical sensors 50 discussed herein comprise the LR-W Series, full-spectrum sensors available from Keyence. In other embodiments, optical sensors 50 can comprise a vision sensor or vision inspection system which grab an image and exploit any of a number of pattern matching tools to form a judgement on the presence of the sealing sticker. Other types of optical sensors that can be programmed to perform one or more of the functions described herein can also be used.

In one embodiment of the present invention, means are provided for adjusting the position of optical sensor 50A in one dimension. Similarly, means are also provided for adjusting the position of optical sensor 50A in two dimensions. By way of example and not by limitation, as depicted in FIG. 3 a support rail 52 having a first end 54 coupled to first side wall 18 and a second end 56 coupled to second side wall 20. An elongated slot 58 passes through support rail 52 along the length thereof. Threaded shafts 60 project from optical sensor 50A and pass through slot 58. Knobs 62 are threaded onto shafts 60. When knobs 62 are tightened against support rail 52, optical sensor 50A is secured in place along the length of support rail 52. However, as knobs 62 are loosened, optical sensor 50A can be freely slid along the length of support rail 52 for laterally adjusting the position of optical sensor 50A in one dimension between side walls 18 and 20. Once optical sensor 50A is moved to the desired location, knobs 62 can be tightened so as to secure optical sensor 50A in the desired location.

Elongated slots 64 and 65 also extend along the length of side wall 18 and side wall 20, respectively. Again, a threaded shaft 66 projects from each end of support rail 52 and passes through respective slots 64 and 65. Knobs 68 are threaded onto threaded shafts 66. Again, as knobs 68 are threaded onto shafts 66 so as to bias against side walls 18 and 20, support rail 52 is secured in a stationary position. However, as knobs 68 are loosened, each end of support rail 52 can be slid along the length of slots 64, 65, thereby moving optical sensor 50A forward and backward within compartment 36 in a second dimension. Once optical sensor 50A is again in the desired position, knobs 68 are again tightened so as to secure optical sensor 50A in the desired location.

In view of the foregoing, optical sensor 50A can be selectively moved laterally side-to-side and/or front to back within compartment 36 to a desired location, thereby enabling one or two-dimensional movement of optical sensor 50A. It is appreciated that there are a variety of different mechanisms that can be used for positioning optical sensor 50A in one or two dimensions. For example, support rail 52 can be in the configuration of a cylindrical rod, C-shaped channel, or other types of rails. Likewise, other types of clamps or fasteners can be used for connecting optical sensor 50A to the different support rails 52 so that optical sensor 50A can move along the length of support rail 52 between side walls 18 and 20 and then be secured in a desired position. In addition, different types of clamps and fasteners can be used to movably secure the opposing ends of support rail 52 to side walls 18 and 20. In other embodiments, the various slots can be replaced with different types of races, tracks, guideways and the like formed on support rail 52 and/or side walls 18 and 20. In still other embodiments, hydraulic, pneumatic, and gear assemblies can be used to selectively move optical sensor 50A along the length of support rail 52 and/or move support rail 52 along the length of side walls 18 and 20. A robotic arm can also be disposed within compartment 36 which attaches to and selectively moves optical sensor 50A in one, two, or three dimensional movement paths. Other mechanisms can also be used.

Where needed, one or more additional optical sensors 50A can be movably positioned on support rail 52. In additional, one or more additional support rails 52 having one or more additional optical sensors 50A can be mounted to side walls 18 and 20. As such, one, two, three, four or more optical sensors 50A could be movably mounted on base 14 facing up toward inspection floor 28.

Returning to FIG. 2, support structure 16 comprises four vertical supports 74A-D secured to and upstanding from the four corners of inspection floor 28. In turn, four cross bars 76A-D laterally extend between each adjacent pair of vertical supports 74A-D at the upper ends thereof. As such, vertical support 74 and cross bar 76 form a framework which partially bounds an inspection zone 80 disposed above inspection floor 28. In general, inspection zone 80 comprises a front side 82 located at or toward the area between vertical support 74A and 74D; a back side 84 comprising the area located at or toward the area between vertical supports 74B and 74C; an upper side 86 located at or toward the area between cross bars 76A-D; a lower side 88 located at or toward the area directly above inspection floor 28; a left side 90 located at or toward the area between vertical support 74A and 74B; and a right side 92 located at or toward the area between vertical supports 74C and 74D.

In one embodiment, as depicted in FIG. 3, a border wall 96 can be vertically secured between vertical supports 74A and 74B while a border wall 98 can be vertically secured between vertical supports 74C and 74D. Border walls 96 and 98 can be transparent so that packaging box 12 can be visually inspected when disposed within inspection zone 80. In other embodiments, border walls 96 and 98 can be solid, opaque walls or can comprise one or more spaced apart rails, partitions or other structures horizontally, vertically, or otherwise disposed between vertical supports 74A and B and vertical supports 74C and D. In still other embodiments, border walls 96 and 98 can be eliminated.

Disposed within inspection zone 80 is an optical sensor 50B. Optical sensor 50B can also be programmed to detect the presence of sealing stickers located on packaging box 12 when packaging box 12 is supported on inspection floor 28 of housing 13. Optical sensor 50B can comprise the same optical sensors as optical sensor 50A, as discussed herein, and can be programmed to perform the functions as discussed herein.

As with optical sensor 50A, the present invention also includes means for moving optical sensor 50B in one dimension and/or two dimensions. By way of example and not by limitation, a support rail 104 extends between cross bars 76A and 76C and has a central longitudinal slot 106 which passes therethrough and extends along the length thereof. Again, threaded shafts 108 upwardly project from optical sensor 50B, pass through slot 106 and have knobs 110 threadedly coupled thereto. By loosening knobs 110, optical sensor 50B can laterally slide along the length of support rail 104 between cross bars 76A and 76C. By tightening knobs 110, optical sensor 50B can be positioned in the desired lateral position.

Furthermore, as depicted in FIG. 3, cross bars 76A and 76C can each be formed with a slot 112 that centrally extends along the length of the top surface thereof. Threaded shafts can project up from support rail 104, through slots 112, and have knobs 114 threadedly coupled thereto. Accordingly, by loosening knobs 114, support rail 104 and optical sensor 50B secured thereto can be moved front to back between cross bars 76B and 76D and by tightening knobs 114, optical sensor 50B can be positioned in the desired location. Accordingly, using the above discussed configuration, optical sensor 50B can be moved laterally side to side in one dimension and/or front to back in a second dimension. The alternatives discussed above or otherwise herein with regard to the means for moving optical sensor 50A are also applicable to the means for moving optical sensor 50B. Where needed, one or more additional optical sensors 50B can be movably positioned on support rail 104. In addition, one or more additional support rails 104 having one or more additional optical sensors 50B can be mounted to cross bars 76A and 76C. As such, one, two, three, four or more optical sensors 50B could be movably mounted on support structure 16 facing toward inspection floor 28.

With reference to FIG. 2, secured to inspection floor 28 are a pair of spaced apart guide rails 118A and 118B. Guide rails 118A and B longitudinally extend between front side 82 and back side 84 of inspection zone 80. Guide rails 118A and B are used to properly align and position packaging box 12 within inspection zone 80. Guide rails 118A and B are configured so that one or both can be laterally moved between left side 90 and right side 92 of inspection zone 80.

By way of example and not by limitation, elongated slots 116A and B longitudinally extend through inspection floor 28 between side walls 18 and 20 of base 14 at front side 82 and back side 84. Again, a shaft or other structure can project down from opposing ends of guide rail 118A and through slots 116A and B. Knobs or other types of retainers can be mounted to the ends of the threaded shafts for selectively securing or permitting movement of guide rail 118A along the length of slots 116A and B. Accordingly, for larger packaging boxes 12, guide rail 118A can be moved towards side wall 18 and for smaller packaging boxes, guide rail 118A can be moved towards guide rail 118B. In other embodiments, guide rail 118B can also move laterally side to side like guide rails 118A. As with the movement of support rail 52, a variety of other structural designs can also be used for lateral movement of guide rail 118A and/or 118B.

As discussed below in greater detail, the present invention also includes a gate 124 that controls movement of packaging box 12 through inspection zone 80 of tamper seal detection system 12. In the embodiment depicted in FIG. 2, gate 124 comprises a rod 126 that is vertically raised and lowered by a regulator 128. Regulator 128 is disposed within compartment 36 of base 14 below back side 84 of inspection zone 80. Regulator 128 can selectively move rod 126 to a closed position as depicted in FIG. 2 where rod 126 is raised and projects into back side 84 of inspection zone 80 and thus prevents packaging box 12 from passing out through back side 84 of inspection zone 80. In turn, regulator 128 can also move rod 126 into an open position as shown in FIG. 3 were rod 126 is retracted from or at least sufficiently retracted from inspection zone 80 so that packaging box 12 can pass out through back side 84 of inspection zone 80. Regulator 128 can comprise an electrical solenoid, pneumatic cylinder, hydraulic cylinder, gear drive assembly, or other drive mechanism that can be used to selectively raise and lower rod 126.

In other embodiments gate 124 can comprise a variety of other structures that selectively block or open back side 84 of inspection zone 80. By way of example and not by limitation, gate 124 can also comprise a door, panel, screen, beam, arm, fence, or other structures that can be designed to selectively block and open back side 84 of inspection zone 80 by collapsing and expanding out, rolling-up and unrolling, pivoting back and forth, sliding side-to-side or up-and-down, or moving in other patterns. It is appreciated that gate 124 is optional and can be eliminated.

Figure 4:
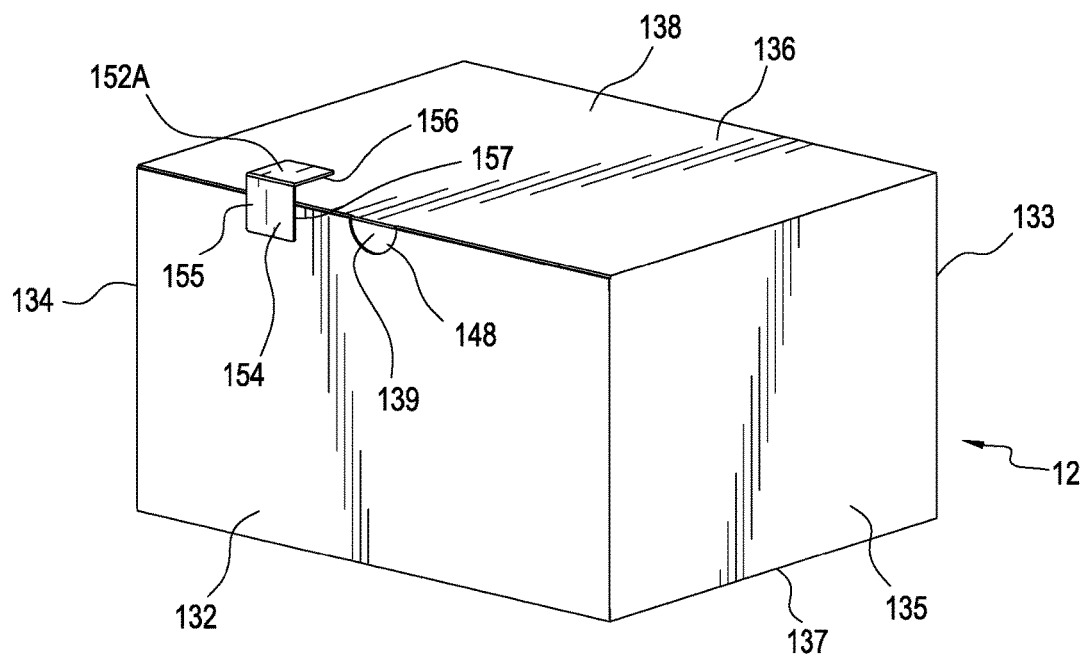
FIG. 4 is a partially exploded top perspective view of the packaging box shown in FIG. 1.

Depicted in FIG. 4 is a top perspective view of packaging box 12. It is appreciated that packaging box 12 can come in a variety of different sizes, shapes and configurations. Packaging box 12 can be comprised of and/or formed from a foldable sheet of material. Specifically, packaging box 12 can be formed as a template that has been cut, such as through a die press or otherwise formed, so that it can be folded and secured into the box shape configuration as depicted in FIG. 4. Packaging box 12 can be comprised of a foldable sheet of material that typically retains a crease when folded. For example, the sheet can comprise a paper-based material, such as paper, cardstock, paperboard or cardboard. In other embodiments, the sheet can be comprised of a synthetic, plastic, or other material (e.g., adapted to retain a crease when folded). The sheet can comprise a single, continuous, unitary structure; a composite; a laminate, an extrusion, or a base sheet having a coating on one or both opposing sides thereof. Packaging box 12 can also be formed of two or more sheets that are connected together, such as through an adhesive or welding. The material for packaging box 12 can have a thickness suitable for various different embodiments. For instance, the material can have a thickness of up to, at least, or about 0.25 mm, 0.5 mm, 1 mm, 1.5 mm, 2 mm, 2.5 mm, 3 mm, and/or 5 mm or between any two of the foregoing. Thicknesses less than 0.25 mm or greater than 5 mm are also contemplated herein. In addition, various components of packaging box 12 may have varying or different thicknesses in some embodiments.

As illustrated in FIG. 4, the final fully assembled and closed packaging box 12 can have a box shaped configuration, i.e., a parallelepiped hexahedron, having square or rectangular panels. Accordingly, the panels of packaging box 12 can be disposed at successive right angles one to another. In other embodiments, packaging box 12 can have other hexahedron or polyhedron configurations or other three dimensional configurations such as cylindrical or conical. As such, an encircling side wall of packaging box 12, discussed below, can have a circular, oval, or other geometric transverse cross sectional configurations.

In one embodiment, tamper seal detection system 10 is designed to be portable so that it can be easily moved between different facilities where blinded trial products are being packaged within packaging boxes 12. To that end, one, two or more handles 130, as depicted in FIG. 1, are disposed on housing 13. In the depicted embodiment, handle 130 is disposed on front wall 20 of base 14. The same handle 130 can also be disposed on back wall 32 to enable easy lifting of tamper seal detection system 10 by one person using two hands. Different configurations of handles can also be used and can be placed different locations on housing 13. Furthermore, tamper seal detection system 10 is typically designed to have a total weight less than 45 kilograms (kg) and more commonly less than 35 kg, 25 kg, or 15 kg.

However, other weights can also be used. To further assist with easy transport, tamper seal detection system 10 is often made having a height H, a width W and a depth D where each of these have a maximum dimension of less than 1.5 meters and more commonly less than 1.25 meters, 1 meter, 0.75 meters or 0.5 meters. Again, depending on use, other dimensions can also be used.

In the depicted embodiment, packaging box 12 has a front panel 132, an opposing rear panel 133, and opposing side panels 134 and 135 extending between the opposing ends thereof. Panels 132-135 combine to form a continuous encircling sidewall 139 that is folded at the corners. Packaging box 12 also has a top closure 136 disposed at the upper end of sidewall 139 and an opposing floor 137 disposed at the lower end of sidewall 139.

Figure 5:
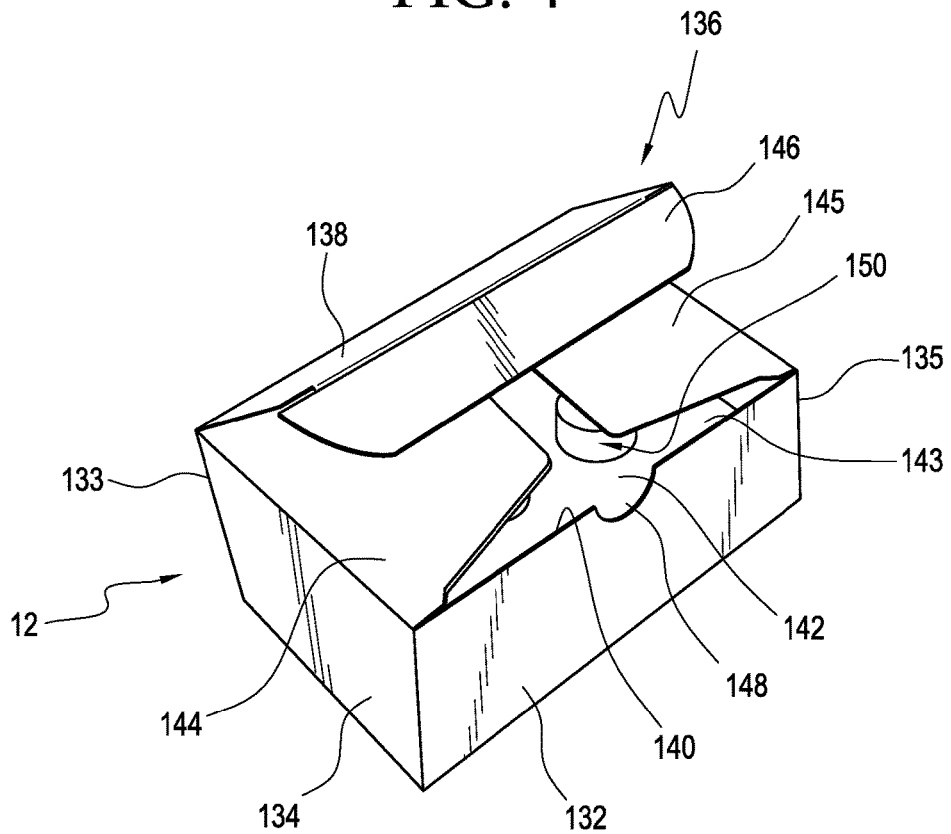
FIG. 5 is a perspective view of the packaging box shown in FIG. 4 with the top closure thereof in an open position.

Top closure 136 and floor 137 will often comprise a plurality of separate panels that interlock, overlap and/or fold together. For example, as depicted in FIG. 5, packaging box 12 has an interior surface 140 that bounds a compartment 142. Compartment 142 has an opening 143 that is bounded by the top edges of panels 132-135. Top closure 136 comprises dust flaps 144 and 145 that project from the top edge of side panels 134 and 135, respectively and can inwardly fold to extend over a portion of opening 143. Top closure 136 also includes a closure panel 138 that projects from a top edge of rear panel 133 and a tuck flap 146 that extends from a free end of closure panel 138. To close opening 143, dust flaps 144 and 145 are initially folded inwardly over opening 143. Closure panel 138 is then folded over opening 143 and extends to front panel 132. Tuck flap 146 is slid into opening 143 so as to be captured between dust flaps 144/145 and front panel 132. Tuck flap 146 assists in keeping closure panel 138 in the closed position as shown in FIG. 4 where opening 143 is covered. A notch 148 can be recessed on the top edge of front panel 132 at a central location for use in gripping and removing tuck flap 146 from opening 143.

Prior to closing top closure 136, a blinded trial product 150 or other desired item is disposed within compartment 142. In at least one embodiment, blinded trial product 150 can comprise one or more different products (e.g., clinical trial materials (CTM)). For example, blinded trial product 150 can comprise a test product which can comprise an active drug product, a comparative drug product, a control drug product, a placebo product, or one or more combinations of the foregoing. Furthermore, in different packaging boxes 12 the active drug product, comparative drug product, control drug product, and/or placebo product can be provided in different quantities, volumes, concentrations, strengths, types (i.e., pill, ointment, liquid, injection, etc.) or combinations of the foregoing. Furthermore, in at least one embodiment, blinded trial product 150 can include multiple dosages or concentrations of one or more different blinded trial products 150. Accordingly, blinded trial product 150 can comprise a plurality of different containers and different container types being placed in the same or different packaging boxes 12. Depending on the form of the drug being tested, the foregoing products may be housed in pill bottles, syringes, vials, tubes or other conventional containers.

Blinded trial product 150 can also comprise one or more support products such as antiseptics, band aids, swabs, gauze, tape, instructions, disposal containers or any other accessories that may be used or associated with the drug being tested. The blind trial product 150 can be held securely within compartment 142 by way of packaging. In some embodiments, "blinded trial products" (or similar terms) can include any clinical trial material (CTM) and does not need to be limited to blinded materials or materials used in blinded trials or studies or components used therein. In other embodiments, any product or combination of products can be housed within packaging box 12.

After top closure 136 is moved to the closed position so that opening 143 is closed, a sealing sticker 152A, as shown in FIG. 4, is applied so as to extend between closure panel 138 and one of panels 132, 134 or 135. In the depicted embodiment, sealing sticker 152A extends between closure panel 138 and front panel 132. Sealing sticker 152A seals closure panel 138 in the closed position so that blinded trial product 150 cannot be accessed or otherwise tampered with without tearing sealing sticker 152. It is appreciated that one, two, three, four or more sealing stickers 152 can be placed at spaced apart locations between closure panel 138 and panels 132, 134 and/or 135.

Sealing sticker 152A comprises an outer layer 154 that is typically comprised of a layer of paper, plastic, metal foil, or another sheet material or composite. Outer layer 154 has an exterior surface 155 and an opposing interior surface 156. A layer of adhesive is applied on interior surface 156 for adhering sealing sticker 152 to packaging box 12. Sealing stickers 152 can have a variety of different sizes, shapes, colors, and material composition. For example, sealing sticker 152A could be square, rectangular, round, elliptical, star shaped, polygonal, have an irregular configuration or have other shapes. Furthermore, a variety of different markings, designs, or other indicia such as bar codes or other identifying indicia can be printed, embossed, affixed or otherwise marked on exterior surface 155 to assist in identifying sealing stickers 152.

In the depicted embodiment, sealing sticker 152A is placed at a perimeter edge of packaging box 12. However, in other embodiments, top closure 136 could be formed from two, three, four or more panels that extend from the top edge of two or more of panels 132-135. These panels can either intersect or overlap centrally over opening 143 so that one or more sealing stickers 152A extend between two or more of the panels at a central location of top closure 136, i.e., inwardly spaced apart from the perimeter edge. In this case, sealing stickers 152A may only extend horizontally as opposed to bending around a corner. In still other embodiments, portions of top closure 136 may extend over the exterior surface of panel 132, 134 and/or 135 so that when sealing stickers 152A extend between top closure 136 and one or more of panels 132, 134 and/or 135, sealing stickers 152A only extend vertically. In still other embodiments, a portion of top closure 136 could wrap around packaging box 12 so as to overlap a portion of floor 137. As such, sealing sticker 152 could be horizontally disposed on or over floor 137. In view of the foregoing, depending on the configuration of packaging box 12, any number of sealing stickers 152 may be used and they may be placed at any desired location on packaging box 12 for sealing packaging box 12 closed.

Figure 6:
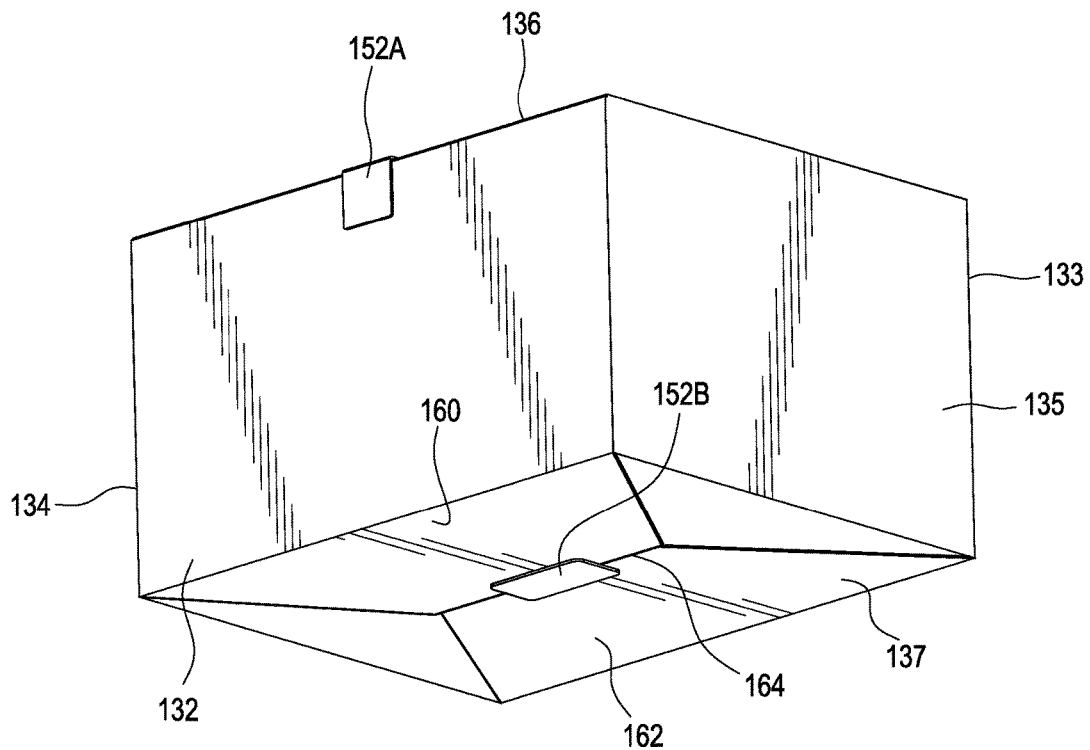
FIG. 6 is a bottom perspective view of the packaging box shown in FIG. 4.

Turning to FIG. 6, as with top closure 136, floor 137 can also comprise a plurality of separate panels that interlock, overlap, and/or fold together. In one embodiment, floor 137 can comprise the same panels and alternatives as top closure 136 discussed above. Likewise, the same one or more sealing stickers 152A can be used to seal floor 137 in the closed position. In the depicted embodiment, however, floor 137 comprises an automatic folding floor that includes two floor panels 160 and 162 each having a generally L-shaped configuration which unfold and centrally interlock when packaging box 12 is moved from a flat collapsed position to an erected expanded position. Further disclose with regard to the automatic folding floor and alternative embodiment for packaging box 12 are disclosed in U.S. patent application Ser. No. 15/128,386, filed Sep. 22, 2016, which is incorporated herein by specific reference.

A sealing sticker 152B passes between floor panels 160 and 162 across a joint 164 centrally formed on floor 137, thereby sealing the floor 137 in the closed position. Sealing sticker 152B can have the same sizes, designs, color, configurations, indicia, composition, and other features as sealing sticker 152A discussed above. Furthermore, depending on the configuration of packaging box 12, sealing stickers 152B used to seal floor 137 closed can be placed at a variety of different locations such as centrally on floor panel 137, around a perimeter edge of floor 137, on the faces of panels 132-135, or even on top closure 136. Furthermore, one, two, three, four or more sealing stickers 152B can be used for sealing floor 137 closed.

Figure 7:
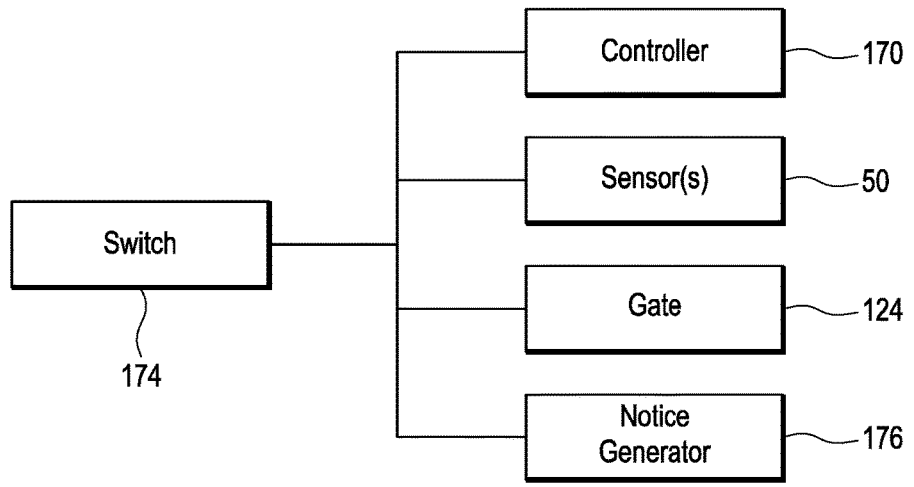
FIG. 7 is a schematic representation of the electronics of the tamper seal detection system depicted in FIG. 1.
Figure 7A:
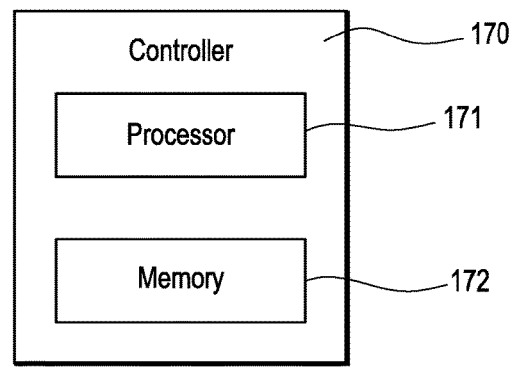
FIG. 7A is a schematic representation of one embodiment of the controller depicted in FIG. 7.

Depicted in FIG. 7 is a schematic representation of one example of electronics that can be used in association with tamper seal detection system 10. The electronics include an electronic controller 170. Controller 170 comprises a programmable logic controller (PLC) or other types of computers. In other embodiments, as depicted in FIG. 7A, controller 170 can comprise a computer processor 171 which operates in conjunction with computer memory 172, such as non-transitory memory. A PLC can also operate in conjunction with separate memory 172. Other types of electronic controllers that can perform the functions discussed herein can also be used. Controller 170 can be either preprogrammed, such as by being hardwired, or can be operated by executing executable code loaded within memory to perform the functions discussed herein. Memory 172 can also be used for storing data generated from sensors 50. Also electrically coupled with controller 170 are the one or more sensors 50 and gate 124. As discussed below in greater detail, a notice generator 176 can be electrically coupled with controller 170 for generating desired notice signals, such as light or sound. A manual or automatic switch 174 is electrically coupled with controller 170 and can be used for activating the system.

The process of using tamper seal detection system 10 with packaging boxes 12 will now be described. Initially, packaging boxes 12 are typically provided in a flat collapsed state. An operator will then fold the collapsed box into an erected three-dimensional configuration wherein floor 137 is closed but top closure 136 remains open. In other embodiments, packaging box 12 may be provided to the operator in an erected state but with top closure 136 open. A desired blinded trial product 150 is then positioned within compartment 142 of packaging box 12 following which closure panel 136 is moved to the closed position so that the blinded trial products 150 is enclosed within packaging box 12.

Next, the desired number of sealing stickers 152 are then placed on packaging box 12 so that packaging box 12 is sealed closed, i.e., the blinded trial products 150 within packaging box 12 cannot be accessed without tearing a sealing sticker 152. Often the number of sealing stickers 152 necessary to effectively seal packaging box 12 is two, i.e., one sticker for top closure 136 and one sticker for floor 137, as discussed above. However, depending on the size, shape and configuration of packaging box 12, other numbers of sealing stickers 152 may be needed or can be used to effectively seal packaging box 12 closed. For example, in one embodiment only one sealing sticker 152 may be required while in other embodiments three, four, five, or more sealing stickers 152 may be required. In most embodiments, the presence of sealing stickers 152 can be detected by inspecting top closure 136 and floor 137. In other embodiments, however, it may be necessary to inspect one or more of panels 134-135 in addition to or in place of top closure 136 and/or floor 137.

Prior to or after packaging box 12 is sealed closed, tamper seal detection system 10 is adjusted to properly receive packaging box 12 and detect sealing stickers 152. Specifically, as depicted in FIG. 1, guide rails 118A and/or 118B are adjusted, as previously discussed so that packaging box 12 can be slid or otherwise placed directly between guide rails 118A and B so as to rest on inspection floor 28 within inspection zone 80. The variance between the spacing between guide rails 118A and B and the width of packaging box 12 received therebetween is relatively small, i.e., typically less than 3 cm, 2 cm, 1 cm, or 0.5 cm, so that packaging boxes 12 for a set configuration are always placed at substantially the same location within inspection zone 80.

In turn, sensors 50A and 50B are adjusted side-to-side and front-to-back, as previously discussed, so that when packaging box 12 for a set configuration is disposed within inspection zone 80 between guide rails 118A and B, sensors 50A and 50B are sufficiently aligned with corresponding sealing stickers 152 so that sealing stickers 152 can be detected by sensors 50A and 50B. Sensors 50 can be vertically aligned over or under a corresponding sealing sticker 152 or angled so as to be directed to a sealing sticker 152. Depending on the proximity of sealing stickers 152, a single optical sensor 50 may be sufficient to detect two or more sealing stickers 152. Otherwise, additional sensors 50 will need to be added and properly adjusted so as to be at least sufficiently aligned with the other sealing stickers 152.

Controller 170 is programmed to determine whether the area visually inspected by optical sensor 50 contains a sealing sticker 152. This is typically accomplished by controller 170 determining whether the area visually inspected by optical sensor 50 contains an object having a size, shape, color, markings, and/or other predefined characteristics that match corresponding pre-programmed characteristics of sealing sticker 152. Other programming methods can also be used. Accordingly, optical sensors 50 can also be used to discern between sealing stickers having different size, shape, color, markings, and/or other predefined characteristics.

In addition to or in place of the foregoing, controller 170 acting with sensors 50 can also be programmed to detect if sealing stickers 152 are in a desired orientation or location. For example, to ensure that there is no differentiation between packaging boxes 12 which could influence the blinded testing, it can be desired that all sealing stickers 152 be placed at the exact same location on each packaging 12 within a predefined tolerance, i.e., each sealing sticker be placed within the same predefined area of each packaging box 12. Likewise, where sealing stickers 152 are non-symmetrical or have non-symmetrical indicia thereon, it can be desired that all sealing stickers 152 are placed at the same orientation within a predefined tolerance, thereby again ensuring no differentiation between packaging boxes 12. Controller 170 acting with sensors 50 can be programmed to determine if sealing stickers 152 that are being detected satisfy the location and/or orientation requirements and can fail to open gate 124 if the conditions are not met. Controller 170 can also be used to count and record the number and type of sealing stickers 152 located on each specific packaging box 12.

For example, once tamper seal detection system 10 is properly adjusted and calibrated to inspect a batch of packaging boxes 12 having a set configuration, a sealed packaging box 12 is manually or automatically placed within inspection zone 80 between guide rails 118 so as to rest on transparent panel 42 of inspection floor 28. This is typically accomplished by passing the packaging box 12 through front side 82 of inspection zone 80. During this initial positioning, gate 124 is in a closed position so that packaging box 12 cannot pass out of inspection zone 80 through back side 84. In one embodiment, gate 124 is positioned so that packaging box 12 is butted against gate 124 when positioned on inspection floor 28, thereby further ensuring that packaging box 12 is always properly positioned.

After or as packaging box 12 is properly positioned within inspection zone 80, switch 174 is activated which causes sensors 50 operating with controller 170 to optically sense or inspect defined areas on packaging box 12 and detect whether the sealing stickers 170 are present in the desired locations, i.e., controller 170 determines whether the preprogram sealing sticker characteristics are present. Switch 174 can be a manual switch or can be automatic based on either sensor 50 or some other sensor or detector determining that a packaging box 12 is disposed within inspection zone 80.

Controller 170 with sensors 50 can detect whether the desired number of sealing stickers 152 are present on packaging box 12 and if they are at desired locations. In addition, each packaging box 12 could include a unique identifier, such as a bar code, printed indicia or other identifier, that is disposed directly on the packaging box 12 or on a sealing sticker 152 or other sticker placed on packaging box 12. Sensors 50 or other types of scanners or sensors could then be used to record that the specific packaging box was scanned and also record data detected from the scan, i.e., record the number, type, placement, orientation, color, configuration and/or other characteristics of sealing stickers 152 or other stickers or indicia on packaging box 12.

Once it is determined that packaging box 12 satisfies predefined conditions, i.e., the proper number and/or type of sealing stickers 152 are located on packaging box 12 at the desired locations and/or orientations, controller 170 can automatically move gate 124 to an open position which allows the operator to remove packaging box 12 through back side 84 of inspection zone 80. This positive result may also be accompanied by notice generator 176 (FIG. 7) emitting a notice signal such as activating a light source or a sound generator. If it is determined that packaging box 12 does not satisfy the predefined conditions, gate 124 is not opened and notice generator 176 may generate a separate notice signal, such as a separate sound, light, or other indication, that designates failure. In this case, the operator is required to remove packaging box 12 through front side 82 of inspection zone 80 where packaging box 12 can then be visually inspected to be determined the cause of the failure. The next packaging box 12 can then be placed within inspection zone 80 and the process repeated.

In view of the foregoing, tamper seal detection system 10 provides a number of unique advantages. For example, detection system 10 helps to reduce or eliminate human error in the inspection process by requiring a highly accurate, computer controlled inspection of each packaging box. Furthermore, the detection system 10 can automatically maintain an ongoing record of the inspection process which enables an operator to easily verify the inspection process. In addition, the inspection process is performed in real time. That is, each packaging box is approved as it is inspected. As such, it should never be necessary to re-inspect all of the sealed packaging boxes based on a missing sealing sticker or miscounted stickers. The system is also easily portable enabling it to be easily set us and used in a variety of different environments. Other benefits also exist.

Figure 8:
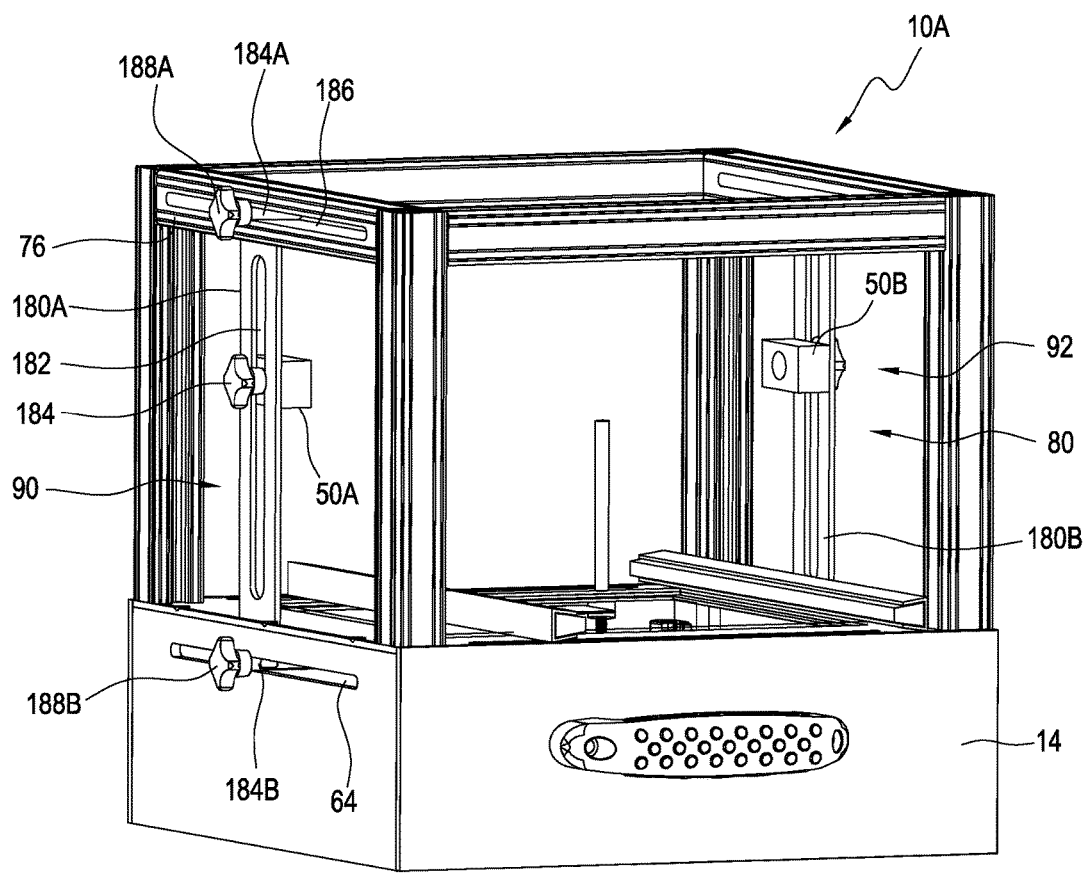
FIG. 8 is a perspective view of an alternative embodiment of a tamper seal detection system where optical sensors are disposed vertically on opposing sides thereof.

Depicted in FIG. 8 is an alternative embodiment of a tamper sealed detection system 10A incorporating features of the present invention. Like elements between tamper sealed detection systems 10 and 10A are identified by like reference characters. The primary distinction between tamper sealed detection systems 10 and 10A is that in detection system 10A, sensors 50 are disposed on left side 90 and rights side 92 of inspection zone 80 as opposed to being disposed vertically above and below inspection zone 80. Specifically, a support rail 180A vertically extends between cross bar 76 and base 14 at left side 90 of inspection zone 80. A slot 182 centrally extends through and along the length of support rail 180A. Optical sensor 50A is attached to support rail 180A by a knob 184 in the same manner as in the prior embodiment so that optical sensor 50A can be vertically adjusted up and down along the length of support rail 180A.

The opposing ends of support rail 180A also have threaded shafts 184A and 184B that pass through a horizontal slot 186 extending along the length of cross bar 76 and horizontal slot 64 extending through base 14, respectively. Knobs 188A and B are selectively coupled to threaded shafts 184A and 184B, respectively. In this configuration, by loosening knobs 188A and B, support rail 180A can also slide horizontally front to back within inspection zone 80. As such, optical sensor 50A can be adjusted both vertically and horizontally for desired alignment with a sealing sticker. Optical sensor 50B is correspondingly mounted on a support rail 180B located on right side 92 of inspection zone 80. As such, optical sensor 50B can also be selectively vertically raised and lowered and move horizontally forward and back within inspection zone 80.

Tamper seal detection system 10A can be used in the same manner as tamper seal detection system 10, as previously discussed, and can have the same alternative embodiments and features thereof. Tamper seal detection system 10A, however, is primarily intended for use with packaging boxes 12 where sealing stickers 152 are located on the sides of packaging boxes 12 as opposed to on the top and bottom thereof. In still other embodiments, however, combinations of tamper seal detection systems 10 and 10A can be provided where sensors 50 are mounted on both opposing sides of inspection zone 80 and above and below inspection zone 80. Furthermore, any desired combinations of the sensor placements can also be used. For example, in one specific embodiment, one sensor 50 may be disposed above or below inspection zone 80 and one sensor 50 disposed on one of the sides inspection zone 80.

Figure 9:
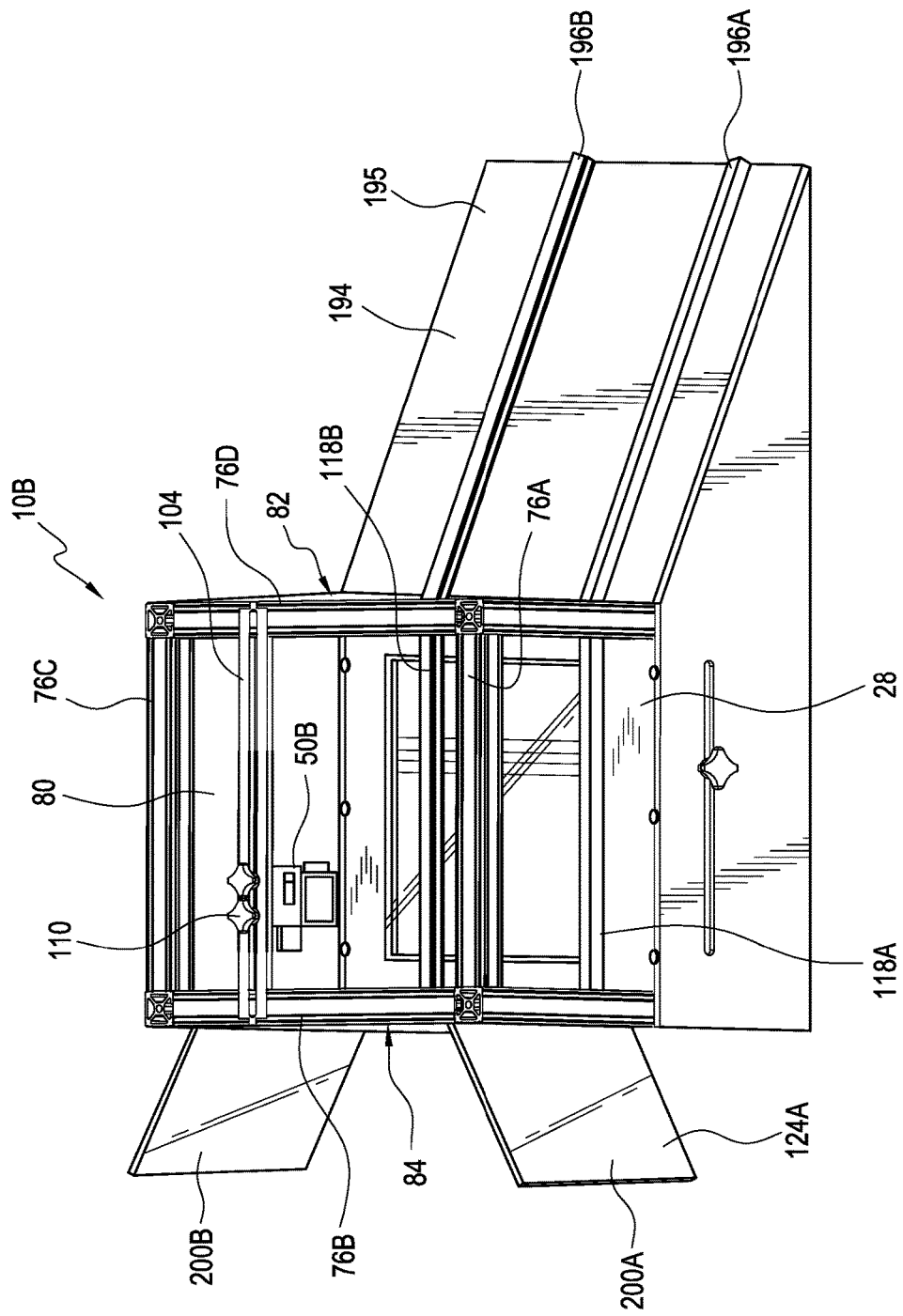
FIG. 9 is a perspective view of an alternative embodiment of a tamper seal detection system having a ramp and a gate that comprises hinged doors.

Depicted in FIG. 9 is another alternative embodiment of a tamper seal detection system 10B incorporating features of the present invention. Again like elements between tamper seal detection systems 10 and 10B are identified by like reference characters and all features and alternative embodiments discussed previously with regard to tamper seal detection systems 10 and 10A are likewise applicable to tamper seal detection system 10B. Tamper seal detection system 10B has a sloped ramp 194 that upwardly extends to inspection floor 28 at front side 82 of inspection zone 80. Guide rails 196A and B extend along a top surface 195 of ramp 194 and match up with rails 118A and 118B, respectively, on inspection floor 28.

As with guide rails 118A and B, one or both of guide rails 196A and B can also be adjusted horizontally so that packaging box 12 can be disposed therebetween within a close tolerance. Ramp 194 enables packaging boxes 12 to be easily slid up ramp 194 and into inspection zone 80. This eliminates the need to individually pick up each packaging box 12 as it is being inserted within inspection zone 80. A similar ramp can also extend down from inspection floor 28 on back side 84 of inspection zone 80 to assist in removing packaging boxes 12 from inspection zone 80.

Another contrast between tamper seal detection systems 10 and 10B is that in detection system 10B, support rail 104 extends between cross bars 76B and D as opposed to between cross bars 76A and C. However, optical sensor 50A can still be equally adjusted forward and backward and/or laterally side to side.

Tamper seal detection system 10B also includes a gate 124A which includes a pair of doors 200A and 200B that pivot between an open position, as shown in FIG. 9, and a closed position where doors 200A and 200B inwardly pivot so as to block back side 84 of inspection zone 80. Accordingly, as with gate 124, gate 124A also functions to prevent a packaging box 12 from passing out of inspection zone 80 through back side 84 until the packaging box 12 is approved by tamper seal detection system 10B as having the proper sealing stickers and/or other markings. Again, a variety of other different configurations of gates can also be used.

Figure 10:
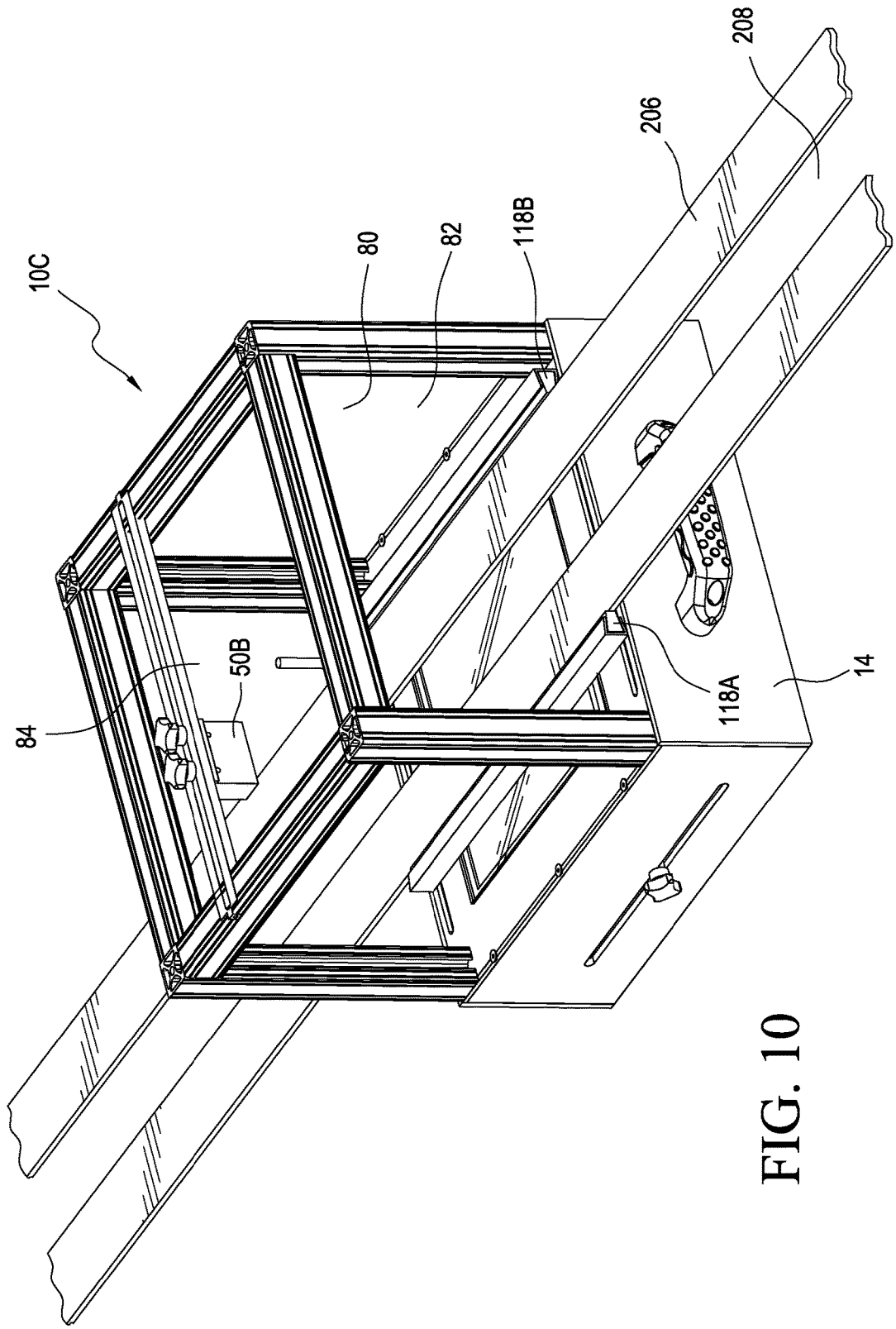
FIG. 10 is an alternative embodiment of a tamper seal detection system having a conveyor belt extending therethrough wherein an elongated slot extends through the conveyor belt.

Depicted in FIG. 10 is another alternative embodiment of a tamper seal detection system 10C incorporating features of the present invention. Tamper seal detection system 10C is the same as tamper seal detection system 10 except that a conveyor belt 206 extends through inspection zone 80 between front side 82 and back side 84. Conveyor belt 206 is disposed between guide rails 118A and B so that when a packaging box 12 is disposed on conveyor belt 206, packaging box 12 can be selectively carried by conveyor belt 206 to the desired location within inspection zone 80 for the detection of sealing stickers 152 by sensors 50. Conveyor belt 206 can be controlled by controller 170 which regulates when and how far conveyor belt 206 moves. As such, convey belt 206 assists in the automated movement of packaging boxes 12 through tamper seal detection system 10.

Figure 11:
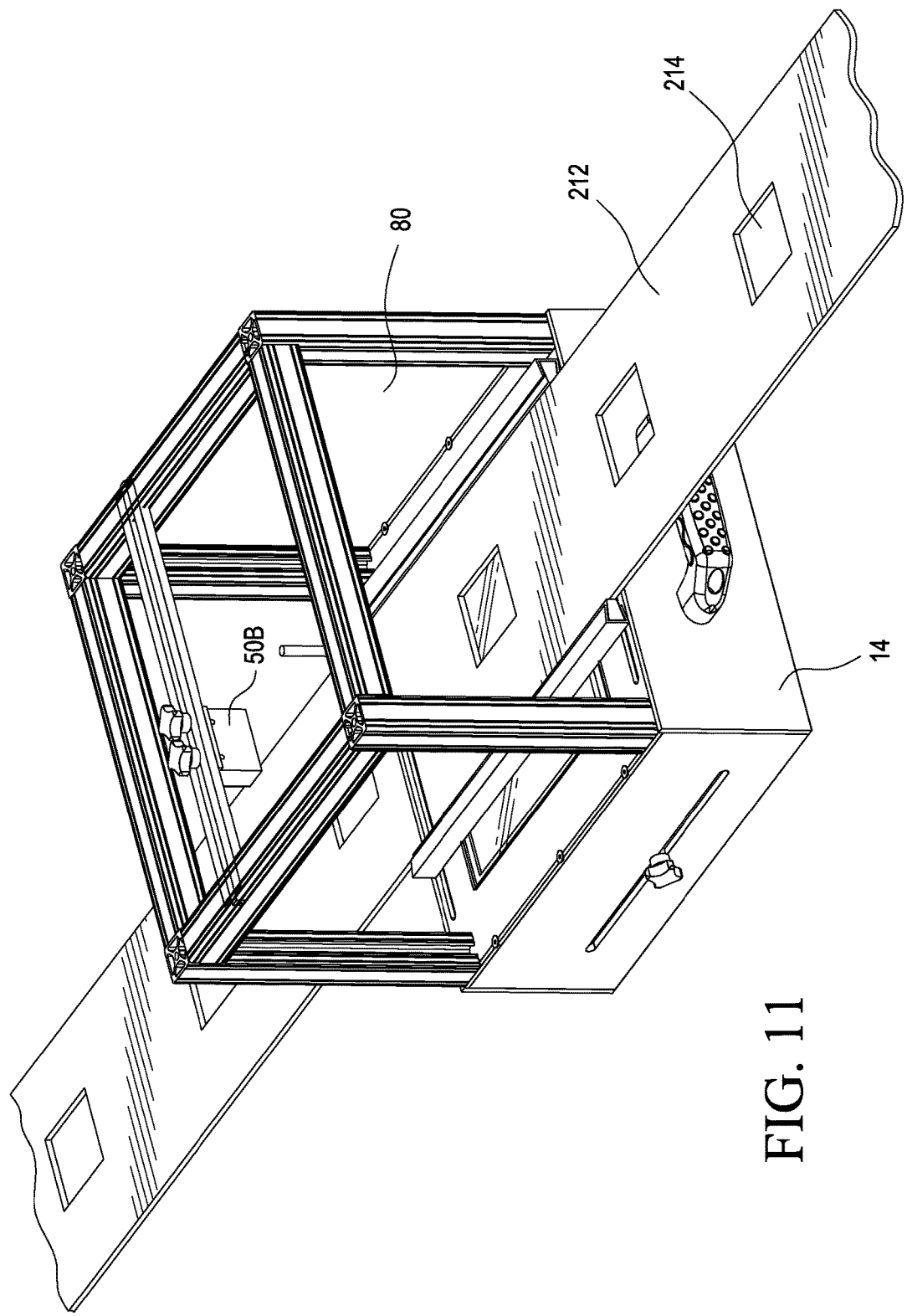
FIG. 11 is a perspective view of an alternative embodiment of a tamper seal detection system having a conveyor belt extending therethrough wherein the conveyor belt has a plurality of spaced apart openings extending therethrough.

Conveyor belt 206 has a slot 208 centrally extending along the length thereof. Slot 208 is configured so that when packaging box 12 is disposed on conveyor belt 206, sealing sticker 152B located on floor 137 (FIG. 6) can still be detected by sensor 50B located within compartment 36 of base 14 (FIG. 3). Where sensor 50B is not required, slot 208 can be eliminated. In contrast to having slot 208 extending continuously along the length of conveyor belt 206, in the embodiment depicted in FIG. 11, a conveyor belt 212 is used passing through inspection zone 80 and having a plurality of spaced apart openings 214 extending therethrough. Again, openings 214 are sized so that when packaging box 12 is disposed on conveyor belt 212 over and opening 214, sealing stickers 152B disposed on floor 137 of packaging box 12 can still be detected through openings 214 by optical sensor 50B.

Figure 12:
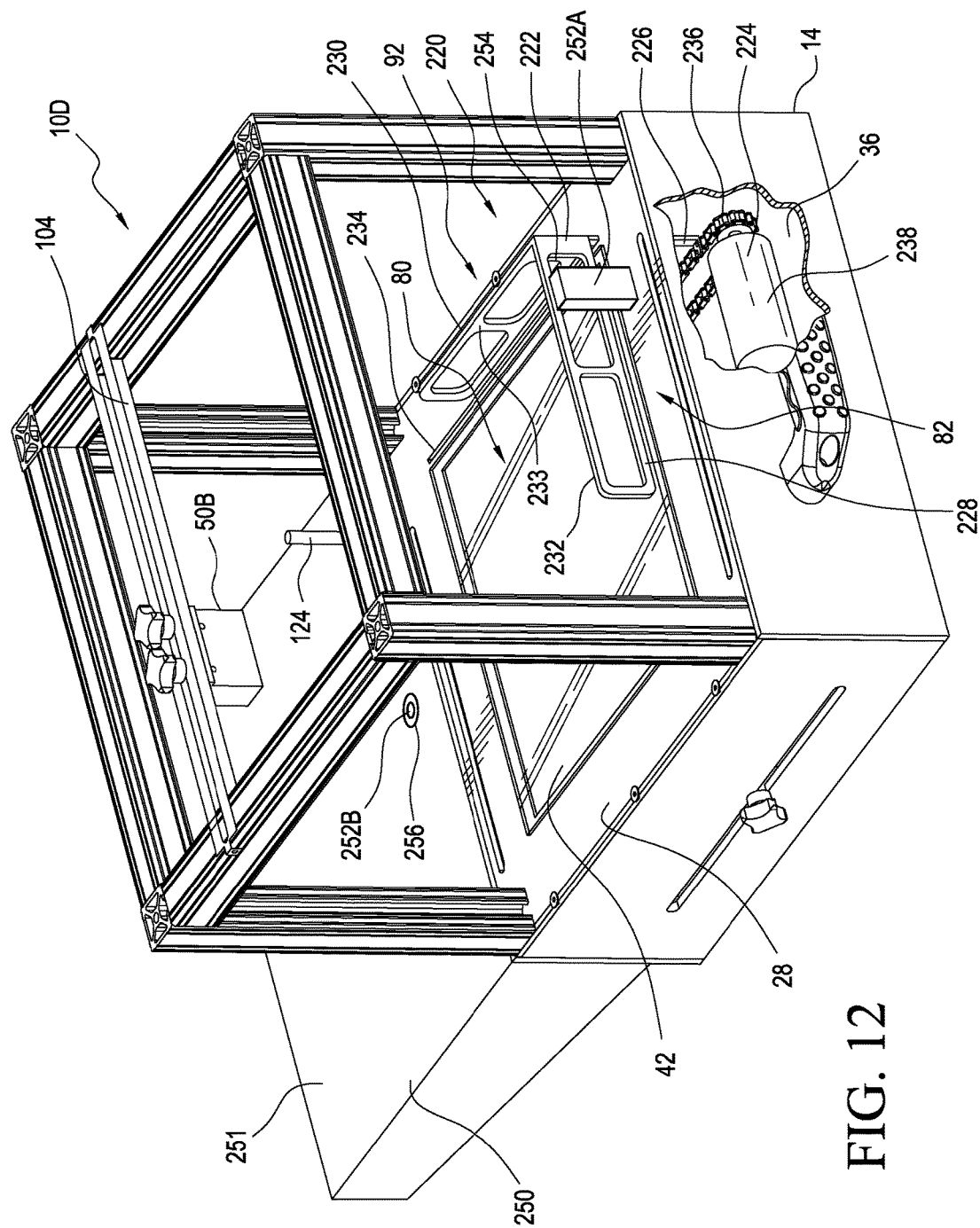
FIG. 12 is a perspective view of an alternative embodiment of a tamper seal detection system having a movable push guide.

Depicted in FIG. 12 is still another alternative embodiment of a tamper seal detection system 10D incorporating features of the present invention. Like elements between tamper seal detection systems 10 and 10D are identified by like reference characters. Furthermore, except where otherwise noted, all of the elements of tamper seal detection system 10, the alternatives discussed relative thereto, and the methods of use, are also applicable to tamper seal detection system 10D. Furthermore, all of the elements and methods of use of tamper seal detection systems 10, 10A, 10B, 10C and 10D can be mixed and matched as needed depending on the desired use. The primary distinction between tamper sealed detection systems 10 and 10D is that in detection system 10D, guide rails 118A and 118B have been removed and replaced with a push guide assembly 220. As discussed below, push guide assembly 220 is used to both align and move packaging box 12.

In general, push guide assembly 220 comprises a push guide 222, a drive assembly 224, and a support 226 that extends therebetween. In the embodiment depicted, push guide 222 comprises an L-shaped body that includes a front arm 228 that extends along front side 82 of inspection zone 80 and a side arm 230 that extends along right side 92 of inspection zone 80. Front arm 228 has an inside front guide face 232 while side arm 230 has an inside side guide face 233. Arms 228 and 230 and guide faces 232 and 233 are orthogonally disposed with at least a portion of inspection zone 80 being disposed therebetween.

Figure 13:
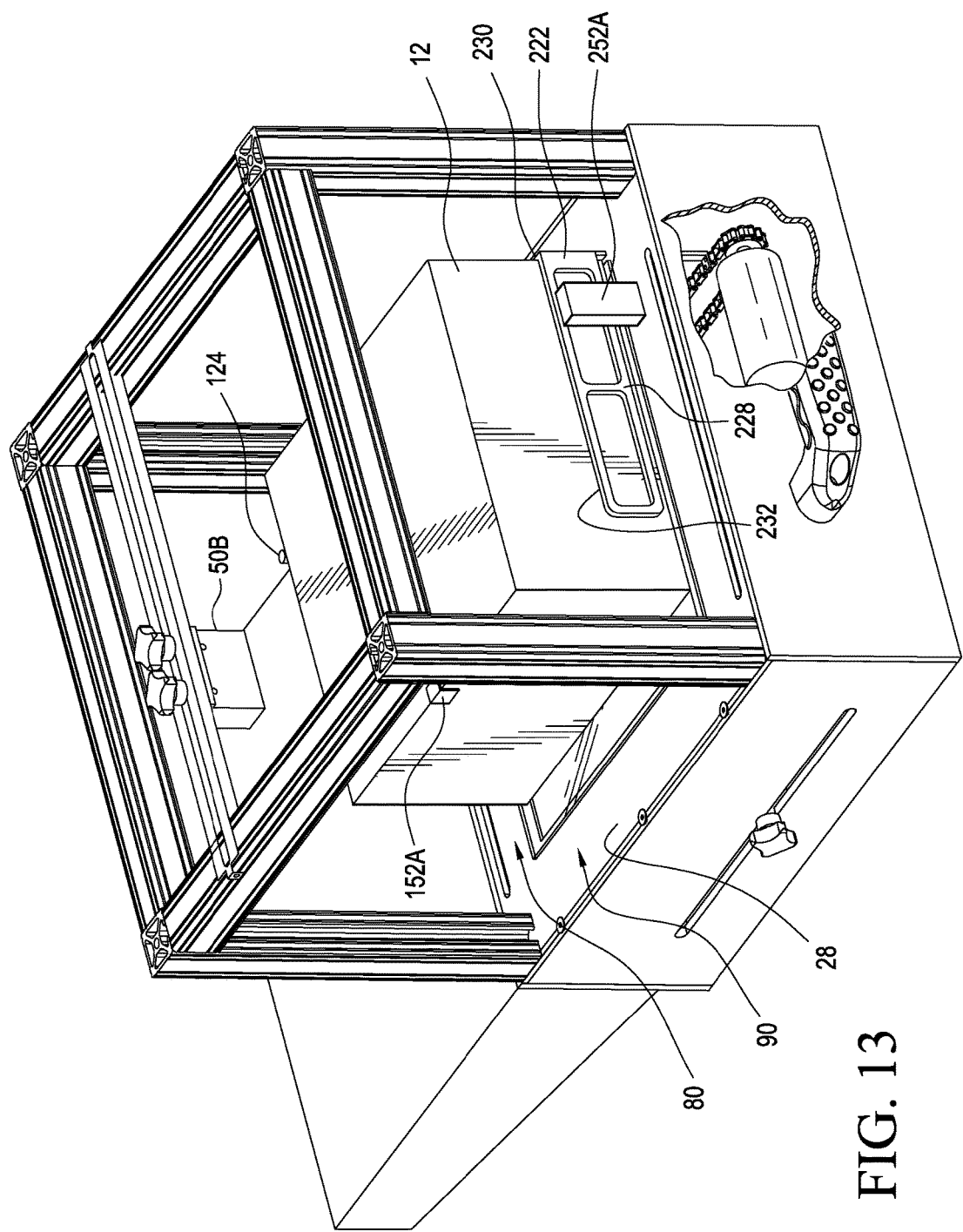
FIG. 13 is a perspective view of the tamper seal detection system depicted in FIG. 12 having a packaging box received therein.
Figure 14:
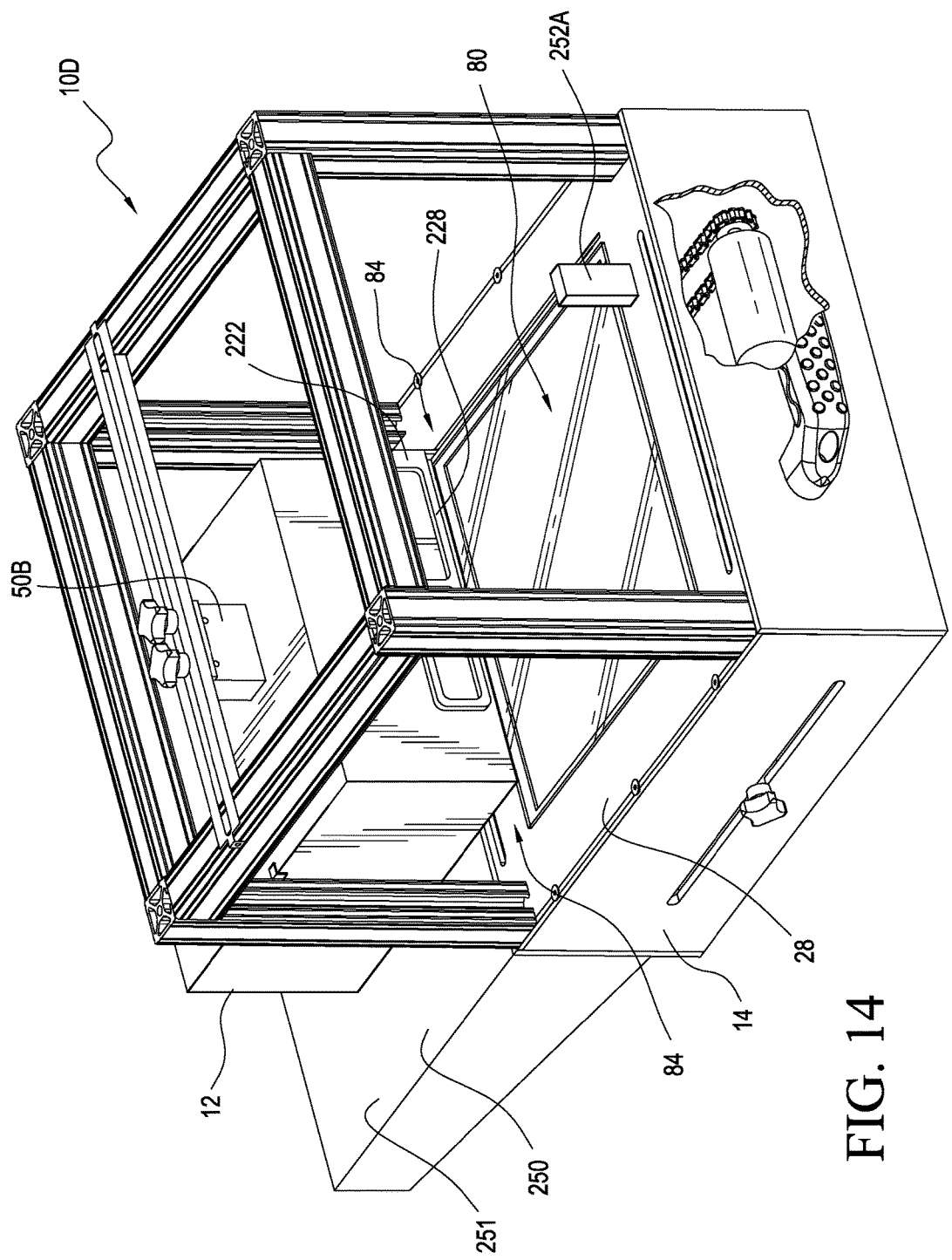
FIG. 14 is a perspective view of the tamper seal detection system depicted in FIG. 13 with the push guide moved to a second position.

Push guide 222 is selectively movable between a first position, as depicted in FIGS. 12 and 13, wherein front arm 228 is disposed at or toward front side 82 of inspection zone 80, and a second position, as depicted in FIG. 14, where front arm 228 is disposed at or toward back side 84 of inspection zone 80. In one embodiment, means are provided for moving push guide 222 between the first position and the second position. By way of example and not by limitation, as depicted in FIG. 12, drive assembly 224 is disposed within compartment 36 of base 14 below inspection floor 28. In this embodiment, drive assembly 224 comprises a driveline 236 that travels along the length of right side 92 of inspection zone 80 below inspection floor 28 and a motor 238 that selectively drives driveline 236 in either a forward or reverse direction.

Driveline 236 can comprise a chain, belt, cable, rope or the like. An elongated slot 234 extends through inspection floor 28 along the length of right side 92 of inspection zone 80 adjacent to transparent panel 42. Support 226 passes through slot 234 and has a first end that connects with push guide 222 and an opposing second end that connects with driveline 236. Support 226 can support push guide 222 slightly above inspection floor 28. As motor 238 moves driveline 236 in a first direction, support 226 moves push guide 222 from the first position to the second position. In turn, when the operation of motor 238 is reversed, support 226 moves push guide 222 from the second position back to the first position.

Figure 15:
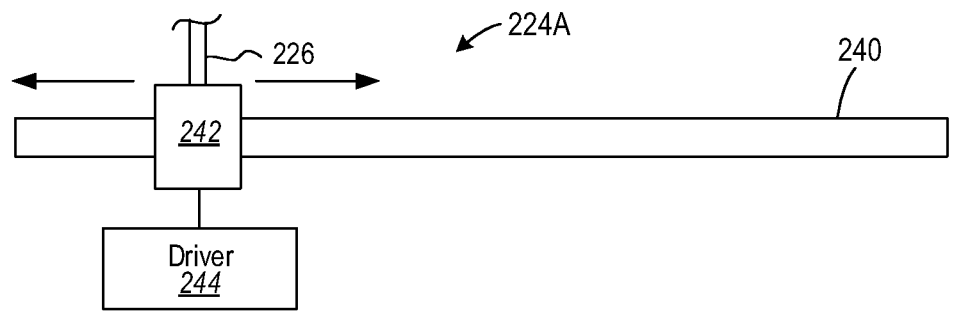
FIG. 15 is an elevated front view of a drive assembly that can be used to move the push guide depicted in FIG. 12.

It is appreciated that drive assembly 224 can have a variety of different configurations that function to move push guide 222 between the first and second positions. For example, depicted in FIG. 15 is an alternative embodiment of a drive assembly 224A that can be used with push guide 222. Drive assembly 224A comprises an elongated track 240 that is supported within compartment 36 of base 14 below inspection floor 28 along right side 92 of inspection zone 80 (FIG. 12). A carriage 242 is mounted on track 240 and can slide back and forth along the length thereof. Support 226 again passes through slot 234 and has a first end connected to push guide 222, as shown in FIG. 12, and an opposing second end connected to carriage 242, as shown in FIG. 15.

A driver 244 functions to selectively move carriage 242 along the length of track 240. For example, driver 244 can comprise pneumatics or hydraulics that control movement of carriage 242. In other embodiments, driver 244 can comprise a gear drive, worm drive, belt drive, chain drive, cable drive, or the like that can be used to control movement of carriage 242. In turn, movement of carriage 242 facilitates movement of push guide 222 between the first position and the second position.

In one specific embodiment, track 240 comprises a hollow tube in which a magnet is disposed. The magnet can freely slide within the tube along the length thereof. Carriage 242 encircles or otherwise couples to the tube so that carriage 242 can freely slide outside of the tube along the length thereof. Carriage 242 is magnetically coupled to the magnet so that as the magnet slides along the length of the tube, carriage 242 slides concurrently with the magnet along the length of the tube. Driver 244 comprises a two-way pneumatic cylinder having gas lines that couple to the opposing ends of the tube. A gas source, such as a compressor, feeds gas to the pneumatic cylinder. Accordingly, when the two-way pneumatic cylinder is in a first position, a pressurized gas is delivered to a first end of the tube that pneumatically pushes the magnet, and thus carriage 242, toward the second end of the tube. In turn, when the two-way pneumatic cylinder is switched to a second position, the pressurized gas is delivered to the opposing second end of the tube that pneumatically pushes the magnet, and thus carriage 242, toward the first end of the tube.

Movement of carriage 242 facilitates concurrent movement of push guide 222 between the first and second positions, as discussed above. A regulator can be coupled with the gas lines and/or the two-way pneumatic cylinder to control the pressure of the gas being delivered. The gas pressure controls the speed at which push guide 222 moves and the force that push guide 222 can exert on packaging box 12. Other drive assemblies 224 can also be used to control movement of push guide 222. Furthermore, it is appreciated that drive assembly 224 need not be located below inspection floor 28. Rather, drive assembly 224 can be located to the side of push guide 222 or above push guide 222.

Returning to FIG. 12, a platform 250 can be formed projecting from the rear of base 14 onto which packaging box 12 can be pushed. Platform 250 has a support floor 251 that is typically flush with inspection floor 28. As also shown in FIG. 12, a first optical sensor 252A is mounted on inspection floor 28 adjacent to push guide 222 so that optical sensor 252A can detect when packaging box 12 is placed within inspection zone 80. More specifically, first optical sensor 252A is shown mounted on inspection floor 28 in front of front arm 228 and in alignment with an opening 254 passing through front arm 228. Optical sensor 252A can thus detect through opening 254 when packaging box 12 is disposed within inspection zone 80 and particularly when packaging box 12 is butted against front arm 228.

As discussed below in more detail, optical sensor 252A only needs to be capable to detecting the presence of packaging box 12. In one embodiment, optical sensor 252A can comprise a proximity sensor and, more specifically, a photoelectric proximity sensor. The photoelectric proximity sensor can be of the reflective, thru-beam, or retroreflective type. One specific example of a photoelectric proximity sensor that can be used in the present invention is the WT150-P460 sensor available from Sick AG. In other embodiments, optical sensor 252A can comprise the same sensors used for optical sensors 50, discussed above. For example, optical sensor 252A can comprise a luminescence sensor or a vision sensor. Other types of optical sensors that can be programmed to perform the functions described herein can also be used.

It is appreciated that optical sensor 252A could also be placed at other locations and still detect the presence of packaging box 12 in inspection zone 80. For example, optical sensor 252A could be mounted on inspection floor 28 on the outside of side arm 230 so as to be in alignment with an opening extending through side arm 230. Likewise, optical sensor 252A could be disposed within compartment 36 (FIG. 3), such as on support rail 52, like optical sensors 50A, so as to sense up through transparent panel 42. In addition, optical sensor 252A could be disposed above inspection zone 80, such as on support rail 104, like optical sensor 50B, so as to sense down into inspection zone 80.

Continuing with FIG. 12, a second optical sensor 252B, which can be of the same type as optical sensor 252A discussed above, is disposed below support floor 251 of platform 250 so that it senses up through an opening 256 extending through support floor 251. Optical sensor 252B and opening 256 are positioned so that when packaging box 12 is pushed onto support floor 251 by push guide 222, packaging box 12 will be disposed over or at least adjacent to optical sensor 252B so that optical sensor 252B can detect the presence thereof. If desired, optical sensor 252B could also be placed at other locations such as on top of support floor 252 but out of the path that packaging box 12 moves.

Figure 16:
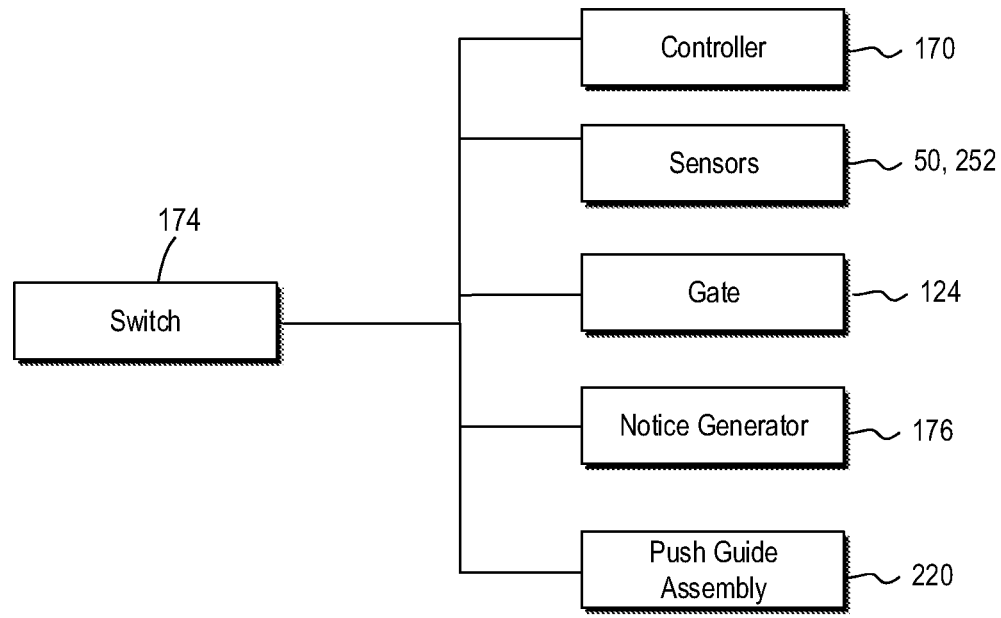
FIG. 16 is a schematic representation of the electronics that can be used with the tamper seal detection system depicted in FIG. 12.

Depicted in FIG. 16 is a schematic representation of one example of electronics that can be used in association with tamper seal detection system 10D. The depicted electronics are the same as that previously discussed in association with FIGS. 7 and 8 except that controller 170 is now also in communication with push guide assembly 220 and optical sensors 252A and 252B. It is appreciated that all of the disclosure, alternatives, and uses of the electronics previously discussed with regard to FIGS. 7 and 8 in association with tamper seal detection system 10 are also applicable to use with tamper seal detection system 10D. Likewise, optical sensors 252A and 252B and their uses associated with tamper seal detection system 10D can also be incorporated into and used in the same way with tamper seal detection system 10.

Tamper seal detection system 10D operates similarly to tamper seal detection system 10. Initially, the electronics of FIG. 16 are activated such as by plugging in the system or turning on switch 174. Once packaging box 12 is prepared and sealed closed with sealing stickers 152, as previously discussed, packaging box 12 is disposed against push guide 222, as depicted in FIG. 13. Specifically, packaging box 12 is advanced through left side 90 of inspection zone 80 and placed on inspection floor 28 with one of the faces of packaging box 12 being butted against front guide face 232 of front arm 228 and an adjacent face of packaging box 12 being butted against side guide face 234 of side arm 230 (FIG. 12). As needed, sensors 50A and 50B (FIG. 3) can be adjusted, such as in at least one or two dimensions, as previously discussed, to be in alignment with corresponding sealing stickers 152 on packaging box 12. With sensors 50A and 50B properly positioned, push guide 222 can be used to quickly and repeatedly position consecutive packaging boxes 12, of the same configuration, in inspection zone 80. That is, packaging boxes 12 are self-centered or aligned in inspection zone 80 by simply pushing the sides of packaging box 12 against front guide face 232 and side guide face 233 of push guide 222.

As packaging box 12 is positioned in inspection zone 80 by using push guide 222 as a guide, optical sensor 252A automatically detects the presence of packaging box 12. Optical sensor 252B (FIG. 12) is also sensing whether a packaging box 12 is disposed on support floor 251. Concurrently, optical sensors 50A and 50B (FIG. 3), operating with controller 170, optically sense or inspect defined areas on packaging box 12 located within inspection zone 80 and detect whether the sealing stickers 170 are present in the desired locations and/or have predefined characteristics.

That is, optical sensors 50 can be used in the same way as previously discussed with regard to tamper seal detection system 10 to determine if the sealing stickers 170 are present and/or if other conditions such as number, type, placement, orientation, color, configuration and/or other characteristics are satisfied. Related information can also be recorded, as previously discussed.

Once it is determined that optical sensor 252A detects packaging box 12 in inspection zone 80, that optical sensor 252B does not detect a packaging box 12 on platform 250, and that optical sensors 50A and 50B detect sealing stickers 152 and/or other predefined conditions thereof, controller 170 automatically moves gate 124 to the open position and controller 170 signals to push guide assembly 220 to move push guide 222 to the second position, as shown in FIG. 14. If the above conditions are not satisfied, push guide 222 and gate 124 are not moved.

As push guide 222 moves to the second position, packaging box 12 is moved at least partially out of inspection zone 80 through back side 84 thereof. In one embodiment, packaging box 12 is moved completely out of inspection zone 80 and is disposed over optical sensor 252B (FIG. 12) so that packaging box 12 is detected by optical sensor 252B. To help ensure that detection system 10D is operating properly, the movement of packaging box 12 can be timed. That is, the time between when push guide 222 starts to move toward the second position and when optical sensor 252B detects packaging box 12 can be measured. If the measured time falls outside of a predefined condition, e.g., falls outside of a predefined time range or limit, a fault can be triggered, causing detection system 10D to stop.

After push guide 222 reaches the second position, push guide 222 automatically returns to the first position. Push guide assembly 220 can be designed to push packaging box 12 past gate 124 so that once push guide 222 is returned to the first position, gate 124 can automatically be moved to the closed position. In the depicted embodiment, however, to help minimize the size of the system, push guide assembly 222 is designed so that as push guide 222 is moved to the second position, packaging box 12 is moved out of inspection zone 80 so that a new packaging box 12 can be placed therein but the initial packaging box 12 is not moved past gate 12. Rather, the initial packaging box 12 is positioned so that it obstructs and prevents the closure of gate 12. Accordingly, only after packaging box 12 is removed from platform 250, either manually or through some automated process, so that packaging box 12 is no longer detected by optical sensor 252B, does gate 124 automatically move back to the closed position.

Once push guide 222 is returned to the first position, a new packaging box 12 can be positioned in inspection zone 80 and butted against push guide 222, as discussed above. The above process can then be repeated. The positioning of the new packaging box 12 can be accomplished even if the prior packaging box 12 remains disposed over optical sensor 252B and gate 124 is in the open position. In the situation where the second packaging box 12 is inserted in inspection zone 80 before the first packaging box 12 is removed from platform 12, once the conditions of optical sensor 252A detecting the presence of the second packaging box 12 and optical sensors 50A and 50B detecting sealing stickers 152 are satisfied, controller 170 can be programmed to signal push guide 222 to push the second packaging box 12 to the second position, without moving gate 124 to the closed position, as soon as optical sensor 252B no longer detects the first packaging box 12. This programming avoids the processing delay of having to wait for gate 124 to move to the closed position and then back to the open position before push guide 222 can move to the second position.

A positive inspection by optical sensors 50 and/or optical sensors 252 may also be accompanied by notice generator 176 (FIG. 16) emitting a notice signal such as activating a light source or a sound generator, as previously discussed. If it is determined that packaging box 12 does not satisfy the predefined conditions of optical sensors 50 and/or 252, gate 124 is not opened, push guide 222 is not moved to the second position, and notice generator 176 may generate a separate notice signal, such as a separate sound, light, or other indication, that designates failure. In this case, the operator is required to manually remove packaging box 12, such as through left side 90 of inspection zone 80, where packaging box 12 can then be visually inspected to determine the cause of the failure. The next packaging box 12 can then be placed within inspection zone 80 and the process repeated.

The above described tamper seal detection system 10D and method of use incorporate gate 124. In a further alternative embodiment, however, gate 124 can be eliminated from tamper seal detection system 10D. Thus, failure of optical sensors 50 to detect sealing stickers 152 or other preprogrammed condition can simply be reflected by push guide 222 not moving to the second position, which can, although not required, also be accompanied by a signal from notice generator 176.

It is also appreciated that in other embodiments push guide 222 can have different configurations. For example, in one alternative, side arm 230 could be removed from push guide 222 so that only front arm 228 remains. In this embodiment, guide rail 118B (FIG. 2) could again be placed on inspection floor 28 along right side 92 of inspection zone 80. During use, packaging box 12 would be butted against both front arm 228 and guide rail 118B for proper alignment but only front arm 228 would be used to move packaging box 12 out of inspection zone 80.

Tamper seal detection system 10D has the same benefits as previously discussed with regard to tamper seal detection system 10. In addition, however, tamper seal detection system 10D provides for easier insertion of packaging box 12 into inspection zone 80 and easier alignment therein. In addition, tamper seal detection system 10 provides for automated removal of packaging box 12 from inspection zone 80.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A tamper seal detection system for detecting a sealing sticker on a packaging box, the system comprising:
   a housing having an inspection floor and at least partially bounding an inspection zone, the inspection zone being configured to receive a packaging box having one or more sealing stickers thereon;
   a first sensor configured to detect the presence of a first sealing sticker located on the packaging box when the packaging box is received within the inspection zone, the first sensor being mounted on the housing;
   a push guide assembly comprising a push guide that is at least partially disposed above the inspection floor, the push guide being movable relative to the inspection floor between a first position and a spaced apart second position; and a gate secured to the housing, the gate being movable between a closed position wherein the gate restricts withdrawal of the packaging box from the inspection zone when the packaging box is therein and an open position wherein the packaging box is free to pass out of the inspection zone when the packaging box is therein.

2. The tamper seal detection system as recited in claim 1, wherein when the packaging box is disposed on the inspection floor and biased against the push guide, the push guide moves the packaging box as the push guide is moved between the first position and the second position.

3. The tamper seal detection system as recited in claim 1, wherein the push guide has a rear guide face that butts against a first side face of the packaging box and a side guide face that butts against a second side face of the packaging box when the packaging box is disposed on the inspection floor.

4. The tamper seal detection system as recited in claim 1, wherein the push guide assembly further comprises a drive assembly that moves the push guide between the first position and the second position.

5. The tamper seal detection system as recited in claim 1, wherein at least a portion of the inspection floor is transparent, the first sensor being disposed below the inspection floor.

6. The tamper seal detection system as recited in claim 1, further comprising a second sensor configured to detect the presence of a second sealing sticker located on the packaging box when the packaging box is received within the inspection zone, the second sensor being mounted on the housing.

7. The tamper seal detection system as recited in claim 1, wherein the gate moves from the closed position to the open position as the push guide moves from the first position to the second position.

8. The tamper seal detection system as recited in claim 1, further comprising:

an electronic controller in electrical communication with the push guide assembly and the first sensor, the controller being programmed to perform the following functions:

activating the first sensor to determine whether the first sealing sticker is located on a first side of the packaging box that is located within the inspection zone; and sending a signal to the push guide assembly which causes the push guide to move from the first position to the second position if the first sensor detects the presence of the first sealing sticker.

9. The tamper seal detection system as recited in claim 8, wherein the electronic controller performs the function of generating a notice signal if the electronic controller determines that the sealing sticker is not located on the packaging box.

10. The tamper seal detection system as recited in claim 1, further comprising the packaging box being disposed within the inspection zone, the packaging box being sealed closed by the at least one or more sealing stickers thereon.

11. The tamper seal detection system as recited in claim 1, further comprising a first proximity sensor disposed on the housing.

12. The tamper seal detection system as recited in claim 1, wherein the first sensor is adjustable mounted on the housing so that the first sensor can be moved in three dimensions.

13. The tamper seal detection system as recited in claim 1, further comprising a first guide rail and a laterally spaced apart second guide rail disposed on the inspection floor.

14. The tamper seal detection system as recited in claim 1, wherein the housing has a height, width, and depth each having a maximum dimension of less than 1.5 meters.

15. The tamper seal detection system as recited in claim 1, further comprising a handle mounted on the housing for use in manually carrying the tamper seal detection system.

16. The tamper seal detection system as recited in claim 1, wherein the housing comprises a sloped ramp leading to the inspection zone.

17. The tamper seal detection system as recited in claim 1, wherein the first sensor comprises is a luminescence sensor.

18. The tamper seal detection system as recited in claim 1, wherein an electronic controller is in electrical communication with the gate and the first sensor.

* * * * *